United States Patent [19]

Blacker et al.

[11] Patent Number: 5,443,970
[45] Date of Patent: Aug. 22, 1995

[54] PYRANONES

[75] Inventors: Andrew J. Blacker, Ripon; John Crosby, Altrincham; John A. L. Herbert, Bury, all of England

[73] Assignee: Zeneca Limited, London, England

[21] Appl. No.: 946,193

[22] Filed: Sep. 17, 1992

[30] Foreign Application Priority Data

| Sep. 20, 1991 | [GB] | United Kingdom | 9120110 |
|---|---|---|---|
| Sep. 20, 1991 | [GB] | United Kingdom | 9120133 |
| Sep. 20, 1991 | [GB] | United Kingdom | 9120134 |
| Sep. 20, 1991 | [GB] | United Kingdom | 9120135 |
| Sep. 20, 1991 | [GB] | United Kingdom | 9120137 |
| Sep. 20, 1991 | [GB] | United Kingdom | 9120138 |
| Sep. 20, 1991 | [GB] | United Kingdom | 9120152 |
| Sep. 20, 1991 | [GB] | United Kingdom | 9120153 |
| Sep. 20, 1991 | [GB] | United Kingdom | 9120157 |
| Sep. 20, 1991 | [GB] | United Kingdom | 9120158 |
| Sep. 20, 1991 | [GB] | United Kingdom | 9120173 |
| Jun. 4, 1992 | [GB] | United Kingdom | 9211795 |

[51] Int. Cl.$^6$ ............................................. C12P 17/06
[52] U.S. Cl. .................................... 435/125; 435/280; 549/291
[58] Field of Search ................... 549/214, 292, 291; 435/196, 197, 125, 280

[56] References Cited

U.S. PATENT DOCUMENTS

| 4,061,769 | 12/1977 | Ohno et al. | |
| 4,255,444 | 3/1981 | Oka et al. | 549/292 X |
| 5,166,364 | 11/1992 | Saunders et al. | 549/292 X |

FOREIGN PATENT DOCUMENTS

| 428392 | 5/1991 | European Pat. Off. |
| 0439779 | 8/1991 | European Pat. Off. |
| 1258033 | 12/1971 | United Kingdom |
| 1407317 | 9/1975 | United Kingdom |

OTHER PUBLICATIONS

*Enzyme Nomenclature* 1978, I.U.B. (1979), pp. 232–240.
Carey et al., Adv. Org. Chem. 2nd ed.; Part A: Structure and Mechanisms (1984), pp. 69–76.
M. Fukui, et al., "Beta-Hydroxy-Delta-Lactones as Chiral Building Blocks Involving 1,3-Dihydroxyl Functions. 1. New Strategies for Stereoselective Construction of 2-Methyl-3,5-Dihydroxy Esters", Chemical and Pharmaceutical Bulletin, vol. 38, No. 10, Oct. 1990, pp. 2890–2892.
D. A. Stolze, et al., "Model Studies Towards the Synthesis of Aplysiatoxin. Spiro-Conformational Control on the Reactivity of C2-Oxidised Spiroketals", Tetrahedron Letters, vol. 32, No. 33, Aug. 12, 1991, pp. 4081–4084.
A. M. Bittencourt, et al., "The Natural Occurrence of 6-Styryl-2-Pyrones and Their Syntesis", Tetrahedron, vol. 27 No. 5, Mar. 1971 pp. 1043–1048.
W. C. Groutas, et al., "Substituted 2-Pyrones, 2-Pyridones, and Other Congeners of Elasnin as Potential Agents for the Treatment of Chronic Obstructive Lung Diseases", Journal of Medicinal Chemistry vol. 28, No. 8, Aug. 1985, pp. 1106–1109.

*Primary Examiner*—Howard T. Mars
*Assistant Examiner*—Kimberly J. Kestler
*Attorney, Agent, or Firm*—Cushman, Darby & Cushman

[57] ABSTRACT

A process for the separation of at least one isomer from a mixture of isomers of a tetrahydropyran-2-one, having at least two chiral centres, which comprises selective reaction of at least one isomer with a reagent catalysed by a hydrolase enzyme whereby at least one isomer is preferentially converted into a distinct chemical species from the other isomers so that it is susceptible of separation by an appropriate chemical or physical separation process in which the tetrahydropyranone is of Formula (1):

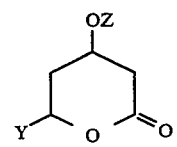

Formula (1)

wherein:
Z is —H or a protecting group susceptible of reaction with the reagent under the influence of the enzyme; and
Y is optionally substituted hydrocarbyl.

14 Claims, No Drawings

PYRANONES

This invention relates to processes for the preparation of tetrahydropyran-2-ones which involve a kinetic resolution stage for producing at least one optically active isomer of a tetrahydropyran-2-one having at least two chiral centres from a mixture of isomers, such as a cis or trans racemate or a mixture of cis and trans racemates, to certain novel isomers, particularly single enantiomers, of the tetrahydropyran-2-one, and to certain novel dihydropyran-2-ones and pyran-2-ones.

Optically active materials such as tetrahydropyran-2-ones may be used as intermediates in the manufacture of compounds such as pharmaceuticals, electronic chemicals and agrochemicals. The optically active tetrahydropyran-2-ones of the present invention are particularly useful as intermediates in the manufacture of HMG-CoA reductase inhibitors. Available processes for the production of these tetrahydropyran-2-ones are typically lengthy, require reagents which are expensive and/or difficult to handle on a large scale, give poor overall yields and do not give access to all optical isomers.

According to the present invention there is provided a process for the separation of at least one isomer from a mixture of isomers of a tetrahydropyran-2-one, having at least two chiral centres, which comprises selective reaction of at least one isomer with a reagent catalysed by a hydrolase enzyme whereby at least one isomer is preferentially converted into a distinct chemical species from the other isomers so that it is susceptible of separation by an appropriate chemical or physical separation process, in which the tetrahydropyran-2-one is of Formula (1):

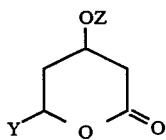

Formula (1)

wherein:

Z is —H or a protecting group susceptible of reaction with the reagent under the influence of the enzyme; and Y is optionally substituted hydrocarbyl.

Z is preferably —H or a readily displaceable protecting group. Examples of suitable readily displaceable protecting groups include —$NO_2$; —PO.($OR^3$)$_2$; —CO.$R^3$; —SO.$OR^3$; and —CO.$OR^3$ in which each $R^3$ independently is optionally substituted alkyl, optionally substituted alkenyl or optionally substituted phenyl. Preferred examples of the protecting group, Z, include, benzoyl, —$COCH_3$, CO(n—$C_3H_7$) and —CO.$OCH_3$.

When Y is optionally substituted hydrocarbyl, it is preferably a $C_{1-3}$-hydrocarbyl, especially $C_{1-2}$-alkyl or $C_{2-3}$-alkenyl, which may, and preferably does, carry one or more, especially 1 to 3, substituents selected from halogen, especially —Cl, —Br, —F or —I; —CN; azide (—$N_3$); —CON(R)$_2$; —OR and —SR; in which each R independently is —H, optionally substituted alkyl, optionally substituted alkenyl or optionally substituted phenyl; —PO.($OR^3$)$_2$, —PO.($R^3$)$_2$, —CO.$R^3$ and —P($R^3$)$_3$+$X^-$ in which $R^3$ is as hereinbefore defined and $X^-$ is halide, preferably chloride or bromide: and —$OZ^1$ in which $Z^1$ is a displaceable protecting group selected from tetrahydropyran-2-yl, alkoxyalkyl, alkoxyalkoxyalkyl, phenylalkyl, triarylmethyl and Si($R^3$)$_3$ in which $R^3$ is as hereinbefore defined or is any of the groups defined above for Z.

Preferred examples of the protecting group $Z^1$ include tetrahydropyran-2-yl, —$NO_2$, methoxymethyl, methoxyethoxymethyl, benzyl, triphenylmethyl, benzoyl, p-tosyl, —$COCH_3$, —CO.$OCH_3$, —$SiMe_3$, —$SiEt_3$, —Si(i-Pr)$_3$, —Si(i-Pr)$Me_2$, —Si(t-Bu)$Me_2$, —Si($CPh_3$)$Me_2$, —Si(t-Bu)$Ph_2$, —Si(i-Pr)$_2$Me, —Si(t-Bu)$_2$Me, —Si($CH_2$Ph)$_3$ and —$SiPh_3$.

It is especially preferred that Y is hydrocarbyl substituted by —$OZ^1$, —CN, —$N_3$, —$OCH_2$Ph, —$SCH_2$Ph, —SH, —OH, —PO.(OPh)$_2$, —PO.(OEt)$_2$, —PO(Ph)$_2$, $PPh_3$+$Br^-$ or —P($CH_2$Ph)$_3$+$Br^-$.

Where R or $R^3$ is or contains an alkyl group this is preferably $C_{1-12}$-alkyl, more preferably $C_{1-6}$-alkyl and especially methyl, ethyl, propyl or butyl. Where R or $R^3$ is or contains an alkenyl group this is preferably $C_{2-12}$-alkenyl, more preferably $C_{2-6}$-alkenyl and especially vinyl or allyl. Where any R or $R^3$ is alkyl or alkenyl it may be in the form of a straight or branched chain.

Where any R or $R^3$ is optionally substituted alkyl or alkenyl, the substituent is preferably selected from $C_{1-6}$-alkoxy; halogen, such as —Cl, —Br or —F; hydroxy; cyano; —$NR_2$; in which R is as hereinbefore defined such as —$NMe_2$; cyclohexyl; phenyl; and protected primary and secondary amino groups such as —NHCOMe and —N($SiMe_3$)$_2$. Where any R or $R^3$ is optionally substituted phenyl, the substituent is preferably selected from $C_{1-6}$-alkyl, especially methyl; $C_{1-6}$-alkoxy, especially methoxy; cyclohexyl; phenyl; nitro; hydroxy; cyano; halogen, especially Cl, Br, or F; —$NR_2$ in which R is as hereinbefore defined such as —$NMe_2$; and protected primary and secondary amino groups such as —NHCOMe and —N($SiMe_3$)$_2$.

Examples of preferred groups represented by Y are —$CH_2$X, —$CHX_2$ or —$CX_3$ in which each X independently is halogen, especially —Cl, —Br, —F or —I; —$CH_2$CN; —$CH_2$CON(R)$_2$; —$CH_2$OR and —$CH_2$SR; —$C_2H_4N_3$; —$CH_2$PO.($OR^3$)$_2$; —$CH_2$PO.($R^3$)$_2$; —$CH_2$P($R^3$)$_3$+$X^-$; —$CH_2OZ^1$; in which $Z^1$, R and $R^3$ are as hereinbefore defined. Where the group represented by Y is —$CX_3$ or —$CHX_2$ the halogen atoms represented by X may be the same or different, thus the same or different halogen atoms may be present in any group, e.g. —$CCl_3$, —$CBr_3$, —$CF_3$, —$CHCl_2$, —$CHBr_2$, —$CCl_2$Br, —$CBr_2$Cl, —$CCl_2$F and —CHBrCl.

Especially preferred groups represented by Y are —$CH_2$OH, —$CH_2$I, —$CH_2$Cl, —$CHCl_2$, —$CHBr_2$, phenylmethoxymethyl—, —$CH_2$CN, —$CH_2$Br, —$CH_2$OSi(t-Bu)$Me_2$, —$CH_2$OSi(t-Bu)$Ph_2$, methoxymethoxymethyl— and methoxyethoxymethoxymethyl—.

The enzyme catalysed reaction is a kinetic resolution which means that the reaction occurs because the enzyme catalyses the reaction of the reagent with different isomers at different rates. A compound with two chiral centres may consist of a mixture of four isomers, i.e. two pairs of enantiomers and a suitable enzyme catalyses reaction of the reagent with each isomer at a different rate so that over a period of time the composition changes from a mixture of, for example 4 isomers to a mixture of 3 isomers and a more distinct chemical species which can be separated from the unchanged isomers by appropriate conventional separation techniques; or one enantiomer of an enantiomer pair is similarly changed to a distinct chemical species which may be similarly separated.

The nature of the reagent and the enzyme depends upon the nature of the group —OZ and the stereochemistry of the isomer(s) with which the reagent is to react. Where Z is —H the selective reaction is conveniently a trans-esterification or esterification and the reagent is an ester or acid capable of reaction with the group —OH when catalysed by the enzyme. In this process the group —OH in the selected isomer(s) is converted into an ester so that the isomer(s) is chemically distinct and can be readily separated from the other isomer(s) in which Z is still H. In this reaction, the enzyme preferably causes the group $R^4CO$— of an ester $R^4COOR^5$ or an acid $R^4COOH$ (in which $R^4$ and $R^5$ each independently is optionally substituted alkyl, alkenyl or aryl) to react preferentially with a group —OH in one, or all except one, isomer in the mixture. It is preferred that the $R^4CO$— portion is preferentially attacked by the group —OH attached directly to the pyran-2-one ring in one, or all except one, of the isomers in the mixture.

The alkyl and alkenyl groups represented by $R^4$ and $R^5$ are preferably $C_{1-18}$-alkyl and $C_{2-18}$-alkenyl, more preferably $C_{1-6}$-alkyl and $C_{2-5}$-alkenyl, especially $C_{1-4}$-alkyl and vinyl and allyl respectively and may be straight or branched chain. The aryl groups represented by $R^4$ and $R^5$ are preferably phenyl or naphthyl each of which may be optionally substituted. Where the groups $R^4$ and $R^5$ are optionally substituted the substituent may be selected from any of those described above for R. $R^5$ is preferably an alkenyl group, more preferably a $C_{2-3}$-alkenyl group and especially vinyl. $R^4$ is preferably an alkyl group, more preferably a $C_{1-4}$-alkyl group and especially methyl, ethyl or n-propyl. The ester of the formula $R^4COOR^5$ may be an alkyl ester, e.g. an alkyl alkanoate, such as methyl acetate, methyl butyrate or ethyl acetate or an alkyl benzoate, such as methyl benzoate, but is preferably a non-reversible acyl donor, especially an alkenyl ester, more preferably an alkenyl alkanoate such as vinyl acetate or vinyl butyrate.

Scheme 1 illustrates a trans-esterification process where the reagent is $R^4COOR^5$ or an esterification process where the reagent is $R^4COOH$ for a mixture of isomers of Formula (1) in which Z is H and Y is as hereinbefore defined:

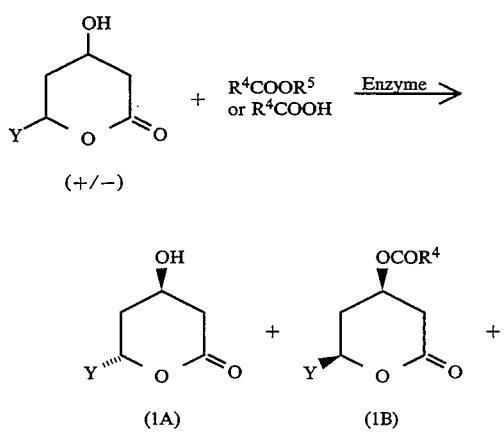

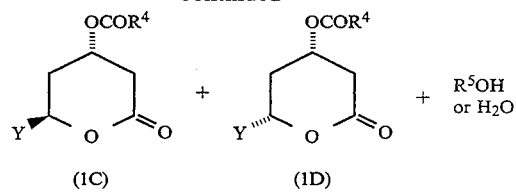

In Scheme 1, Compounds 1B, 1C & 1D are isomeric esters formed by preferential esterification of the corresponding alcohol isomers in the mixed isomer starting material and are distinct chemical species from the unchanged alcohol, Compound 1A. The latter may be separated from the former by any convenient means such as chromatography, solvent extraction, crystallisation or distillation.

The trans-esterification and esterification reactions may be performed in a two phase liquid medium comprising water and an immiscible organic liquid. Where two phases are present the enzyme partitions predominantly into the aqueous phase and thus the enzyme catalysed reaction occurs mainly in the aqueous phase. In the aqueous phase the equilibrium position of the trans-esterification and esterification reactions may be shifted resulting in a decreased yield of the required product although the presence of some water is required for the enzyme to catalyse the reaction. Thus, the trans-esterification and esterification reactions are preferably performed in a single phase organic liquid medium which contains small amounts of water. By small amounts of water it is meant that water immiscible organic liquids contain less than or equal to the amount of water required to saturate the organic liquid and water miscible organic liquids contain less than 50%, preferably less than 20% and especially less than 10% water. When water is present in predominantly organic systems the concentration of water may not be very meaningful and the system may be better defined using the thermodynamic activity of water (Aw). Aw values may be measured via relative humidity in an equilibrated gas phase as described in EP 64855A. Water under standard state conditions has by definition an Aw value of 1. For the trans-esterification reaction the activity of water (Aw) in the organic liquid is less than 1 and greater than 0.05, preferably from 0.95 to 0.1.

The reaction medium may comprise one or more of the participating species, i.e. the tetrahydropyran-2-one or the ester $R^4COOR^5$, or the acid $R^4COOH$ or a substantially inert organic liquid or a mixture of such liquids. Suitable inert organic liquids include a straight or branched chain alkane, especially a $C_{5-16}$-alkane such as hexadecane, iso-octane or hexane; an optionally substituted arene, especially an optionally substituted benzene such as toluene or xylene; an optionally substituted ether, especially a $C_{1-5}$-alkoxy-$C_{1-5}$-alkane such as t-butoxymethane or ethoxyethane; a $C_{4-8}$-cyclic ether such as tetrahydrofuran or 1,4-dioxane; a halogenated alkane, especially a halogenated $C_{1-3}$-alkane such as dichloromethane, trichloromethane, tetrachloromethane or 1,1,2-trichloroethane; a carboxylic acid, especially a $C_{1-3}$-carboxylic acid such as ethanoic or propanoic acid; an alkyl cyanide, especially a $C_{1-3}$-alkylcyanide such as acetonitrile; an alkyl alkanoate, especially a $C_{1-5}$-alkyl $C_{1-5}$-alkanoate such as i-propyl acetate, methyl butyrate or ethyl acetate; an alkyl benzoate, especially a $C_{1-5}$-alkyl benzoate, such as methyl benzoate or ethyl benzoate; an alkenyl alkanoate, especially a $C_{2-5}$-alkenyl $C_{1-5}$-alkanoate such as vinyl acetate or vinyl butyrate; or an optionally branched alkanol, especially a $C_{1-10}$-alkanol, and more especially a $C_{1-6}$-alkanol, such as butan-1-ol, butan-2-ol, t-butanol, propan-2-ol, ethanol or methanol.

Where Z is a protecting group the selective reaction is conveniently a hydrolysis and the reagent is a hydrolytic agent, such as water or an alkanol, ROH in which R is as hereinbefore defined, which is capable of replacing the protecting group Z by H when catalysed by the enzyme. In this process the group OZ in the selected isomer(s) is converted into an OH group so that the selected isomer(s) is/are chemically distinct and can be readily separated from the other isomer(s) in which Z is still a protecting group. In this reaction the enzyme preferably catalyses the hydrolysis of one or more isomers in a mixture of isomers of Formula (1) in which Z is a protecting group, such as —CO.R⁴. Scheme 2 illustrates the hydrolysis of a mixture of isomeric esters of Formula (1) in which Z is —CO.R⁴ and R⁴ and Y are as hereinbefore defined:

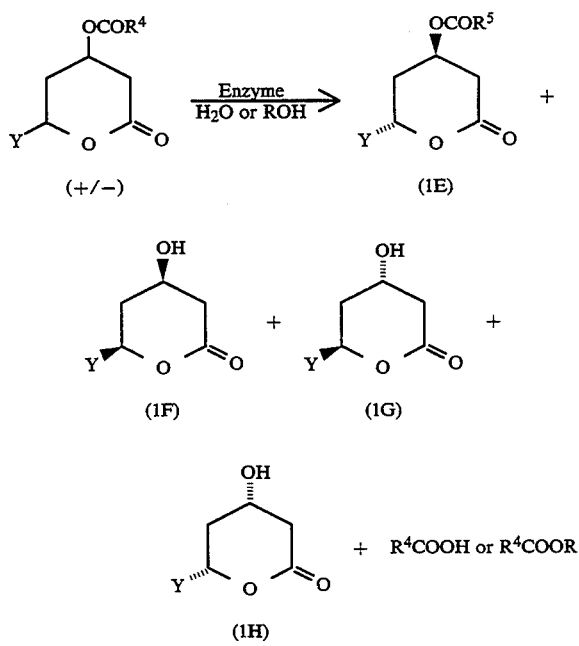

In Scheme 2, Compounds 1F, 1G and 1H are alcohols formed by preferential hydrolysis of a the corresponding isomeric ester in the starting material and is a distinct chemical species from the unchanged isomeric ester, Compounds 1E. The former may be separated from the latter by any convenient means such as chromatography, solvent extraction, crystallisation or distillation. Once separated Compound 1E may be chemically hydrolysed to the corresponding hydroxy compound.

The enzymatic hydrolysis reaction may be performed in a liquid medium such as water, an organic liquid or a mixture thereof. Suitable organic liquids for the hydrolysis are those described above for the trans-esterification. Where the liquid medium comprises water or an alkanol, the water or alkanol may form only a proportion of the liquid medium, e.g. from 1% to 50% thereof, depending on the equilibrium constant for the system, and may be buffered at a pH from 4 to 10, preferably from 4 to 9 and especially from 6 to 8. The buffer may be inorganic or organic and is preferably an inorganic phosphate such as sodium or potassium phosphate or an amine salt, such as the hydrochloride, acetate, phosphate or benzoate salt of tri(hydroxy methylamino)methane.

The reaction medium for the trans-esterification, esterification or the hydrolysis may further comprise components which stabilise the enzyme and maximise its catalytic efficiency. Such components may comprise cations, especially $H^+$ and $H_3O^+$; alkali metal cations such as $Li^+$, $Na^+$ and $K^+$; alkaline earth cations such as $Mg^{2+}$ and $Ca^{2+}$; Group III metal cations such as $Al^{3+}$; transition metal cations such as $Zn^{2+}$, $Fe^{2+}$, $Cu^{2+}$, $Co^{2+}$ and $Ni^{2+}$; and/or ammonium and substituted ammonium cations such as $NR_4^{30}$ in which each R independently is as hereinbefore defined. Other suitable components may comprise anions, especially halides such as $F^-$, $Cl^-$, $Br^-$ and $I^-$; oxyphosphorus anions such as $HPO_4^{2-}$ and $PO_4^{3-}$; oxysulphur anions such as $SO_4^{2-}$; oxynitrogen anions such as $NO_3^-$; $OH^-$; $CO_3^{2-}$ and/or organic anions such as formate, acetate, oxalate, tartrate, malonate or succinate. The preferred cations and anions may be used in combination or as salts with other anions and cations, respectively. Salts containing these ions may be employed undissolved in the reaction medium in order to change the state of hydration and thus the activity of water in the medium. For example when sodium carbonate decahydrate is added to the reaction medium it becomes sodium carbonate monohydrate by losing 9 equivalents of water, in this way a known amount of water may be added to the reaction medium. To this end the salts may be hydrated salts or mixtures of anhydrous and hydrated salts (see Biochim, Biophys Acta (1991) 1078, 326). The hydrolysis medium may also contain antioxidants such as ascorbates or thiols, such as dithiothreitol, 2,3-dimethylpropanethiol, ethanethiol and cysteine.

The trans-esterification, esterification and hydrolysis reactions may be performed at temperatures from 0° C. to 100° C., preferably from 10° C. to 60° C., more preferably at 25° C. to 60° C. and especially from 30° C. to 60° C. During the course of the hydrolysis reaction an inorganic base, preferably an alkali metal hydroxide such as sodium hydroxide, may be added to maintain the pH of the reaction mixture. The reaction medium may be agitated by appropriate methods such as stirring, shaking or sonicating.

The hydrolase enzyme is preferably an esterase, lipase, nitrilase, amidase, peptidase, glycosidase or phosphatase derived from microbial, animal or plant sources. Especially preferred enzymes are Chromobacterium viscosum lipase from Biocatalysts Ltd, AMANO P lipase from Amano Pharmaceuticals Co Ltd (AMANO is a trade mark of Amano Pharmaceuticals), Pseudomonas fluorescens lipase from Biocatalysts or Fluka Chemie, Mucor miehi strains such as NOVO IM60 and NOVO lypozyme from Novo Industrie (NOVO is a trade mark of Novo Industrie) or Lipoprotein lipase from Pseudomonas species from Boehringer Mannheim GmbH or Fluka Chemie AG.

Suitable forms are microbial whole cell preparations or fractions derived from microbial, plant and animal tissues containing the required hydrolase activities. Such fractions include secreted enzymes, broken cells, cell-free extracts and purified hydrolase enzymes. The hydrolase enzyme may be prepared and used in the reaction as a lyophilised solid or water-containing liquid. When the hydrolase enzyme is prepared as a lyophilised solid it may further comprise components to stabilise the enzyme system and maximise its catalytic activity and antioxidants as described above.

The lyophilised solid may further comprise organic additives such as sugars, preferably glucose, mannose or trehalose; or polyols such as polyethyleneglycol; or detergents such as alkylammonium salts or alkylsulphonate salts. The hydrolase enzyme may be coated, for example by passive adsorption, onto an inorganic or organic support material or covalently bonded onto an inorganic or organic support material. The inorganic support material may be a powdered or beaded silicate; an infusorial material, such as diatomaceous earth; zeolite; montmorillonite clay; finely divided carbon such as charcoal; or a polyphosphazene. A preferred inorganic support material is a beaded glass; sand; silica gel; a diatomaceous earth such as CELITE (CELITE is a trade mark of Johns Manville Corporation); a molecular sieve (e.g. 4A); or charcoal. A convenient organic support is a resin such as EUPERGIT C (EUPERGIT is a trade mark of Rohm Pharma) an ionic exchange resin; a polysaccharide; a polyacrylamide; a protein; a nucleic acid; a lipid; a detergent capable of forming micelles; or a liposome. A preferred organic support material is an anionic exchange resin or a cellulosic material such as SEPHAROSE (SEPHAROSE is a trade mark of Pharmacia, Sweden).

The hydrolase enzyme may be prepared for use in the hydrolysis reaction as a stock solution in an aqueous liquid medium containing components which stabilise, maximise its catalytic activity and prevent its oxidation, as described above. The same stock solution may be freeze dried at a temperature from $-70°$ C. under vacuum until almost dry to give a hydrolase enzyme residue which is suitable for use in the trans-esterification reaction. However, it is important that the reaction medium for the trans-esterification reaction contains at least some water otherwise the hydrolase enzyme is ineffective as a trans-esterification catalyst. Thus either the enzyme residue must contain some water or water must be added to the reaction medium.

The compound of Formula (1) in which Z is —H may be prepared by chemical reduction of the corresponding dihydropyran-2-one as described below. The 4-hydroxy group, in the compound of Formula (1) in which Z is H, may be protected by reaction with a compound of formula Z—X (wherein Z is as hereinbefore defined except —H or —$NO_2$ and X is halogen, especially —Cl or —Br). Compounds of Formula (1) where Z is —$NO_2$ as the protecting group may be prepared by reaction of the compound of Formula (1) where Z is mesyl with an alkylammonium nitrate. In compounds of Formula (1) where Y is hydrocarbyl substituted by —OH the —OH may be similarly protected. The compound of Formula (1) in which Y is hydrocarbyl substituted by —$P(R^3)_3{}^+X^-$ may be prepared by reaction of the corresponding compound, in which Y is hydrocarbyl substituted by X (in which X is a replaceable halogen, e.g. Br) and Z is preferably a protecting group, with a trialkyl- or triaryl-phosphine in an organic liquid, such as toluene, at an elevated temperature. A compound of Formula (1) in which Y is hydrocarbyl substituted by one or more halogen atoms, for example —$CH_2X$ or —$CHX_2$, and Z is preferably a protecting group, may be prepared by halogenation of the corresponding compound in which Y is hydrocarbyl, for example —$CH_3$. A compound of Formula (1) in which Y is hydrocarbyl substituted by one or more halogen atoms and $Z^1$ is a protecting group may be prepared by halogenation of the compound of Formula (3) below in which Y is hydrocarbyl followed by reduction to the corresponding compound of Formula (1). A compound of Formula (1) in which Y is hydrocarbyl substituted by azide may be prepared by reaction of the corresponding compound in which Y is hydrocarbyl substituted by —Br and $Z^1$ is a protecting group with sodium azide in a liquid medium such as dimethylformamide.

The preparation of compounds in which Y is hydrocarbyl substituted by —CN, —$OZ^1$, —OR and —SR are described more fully below.

Further details of reactions for preparation of compounds of Formula (1) in which Y is $OZ^1$ and Z and $Z^1$ are protecting groups are described in 'Protective Groups in Organic Synthesis', T. W. Greene and P. G. M. Wuts, published by Wiley & Sons 2nd Edition (1991).

In the reaction stages, apart from the enzyme catalysed reactions, hereinafter described Z may also be any of the less readily removable protecting groups defined above for $Z^1$ where the reaction conditions are such that an easily displaceable protecting group may be lost. In such instances where a less readily removable $Z^1$ group is used to protect a 4-hydroxy compound the $Z^1$ group would be removed and replaced by the readily displaceable groups defined for Z before separating isomers in the enzyme catalysed reaction. Particularly preferred Z groups for protecting a 4-hydroxy compound are benzyl, —$Si(R^3)_3$ in which $R^3$ is as hereinbefore defined, —$CPh_3$, methoxymethyl- and methoxyethoxymethyl-.

The 4-hydroxy compound may be liberated for example from a) a benzyl or a —$CPh_3$ protected 4-hydroxy group by hydrogenation in a liquid medium preferably an alkanol such as methanol in the presence of a hydrogenation catalyst such as palladium on carbon; b) an —$Si(R^3)_3$ protected 4-hydroxy group by reaction with a fluoride, preferably a tetralkylammonium fluoride such as tetrabutylammoniumfluoride in a liquid medium preferably an ether such as diethylether or tetrahydrofuran; c) a methoxymethyl- or methoxyethoxymethyl- protected 4-hydroxy group by reaction with a mixture of thiophenol and $BF_3$.etherate, or a triphenylmethylfluoroborate in a halocarbon such as dichloromethane, or a zinc halide such as zinc bromide in a halocarbon such as dichloromethane. Once the 4-hydroxy compound has been liberated this may be protected with a readily displaceable protecting group, Z, as hereinbefore described.

According to a further feature of the present invention there is provided a process for the preparation of a tetrahydropyran-2-one of the Formula (1):

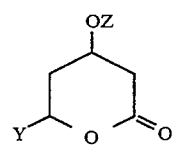

Formula (1)

by reduction of a dihydropyran-2-one of Formula (2):

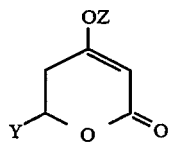

Formula (2)

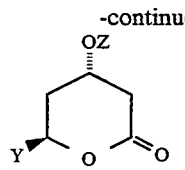

Formula (1L)

wherein Y and Z are as hereinbefore defined.

This process may be performed by chemical reduction, where the dihydropyran-2-one of Formula (2), preferably in a liquid medium, is reacted with hydrogen in the presence of a catalyst. The liquid medium is preferably an organic liquid, and more preferably an alcohol, especially a lower alkanol such as ethanol, n-propanol or isopropanol or water or a mixture of water and a lower alkanol such as water/ethanol or an ester such as ethylacetate or isopropylacetate. Suitable catalysts are metal catalysts preferably those where the metal is from Group VIII of the Periodic Table. The catalyst is preferably a finely divided metal or is a metal carried on a support such as carbon or aluminium oxide. An especially preferred catalyst is Raney nickel. The process is preferably performed at a temperature from 0° C. to 120° C., more preferably from 10° C. to 80° C. and especially from 20° C. to 50° C. The process is conveniently carried out at the boiling point of the liquid medium and at a pressure from $1 \times 10^4$ Pa to $1 \times 10^6$ Pa, preferably from $5 \times 10^4$ Pa to $5 \times 10^5$ Pa and especially from $8 \times 10^4$ Pa to $2 \times 10^5$ Pa. The process is preferably continued until substantially all the starting material is consumed which may be detected by chromagtographic analysis. The product may be isolated by removing the catalyst by filtration and evaporation of the liquid medium. The product may be purified by any convenient means such as distillation or crystallisation.

Where dihydropyran-2-ones of Formula (2) are already optically resolved at the 6-position chemical reduction of the double bond between the 3- and 4-positions with cis- or trans-control fixes the stereochemistry at the 4-position and individual enantiomers can be obtained. For example with cis-control enantiomers of Formulae (1J) or (1K) are obtained and with trans-control, enantiomers of Formulae (1I) or (1L) can be obtained. However, where dihydropyran-2-ones of Formula (2) are racemic, chemical reduction with no cis-trans selectivity, produces a mixture of isomers of Formulae (1I), (1J), (1K) and (1L):

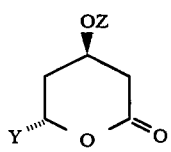

Formula (1I)

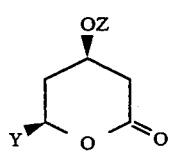

Formula (1J)

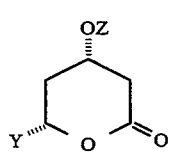

Formula (1K)

Separation of a mixture of isomers of Formulae (1I), (1J), (1K) and (1L) may be achieved by reacting the mixture with optically active α-methylbenzylamine to form the corresponding diasteromeric α-methylbenzylamide derivatives. The α-methylbenzylamide derivatives may be separated by any convenient means such as chromatography or crystallisation. After separation each α-methylbenzylamide derivative is firstly hydrolysed and then dehydrated to reform the individual isomers of Formulae (1I) to (1L).

According to a further feature of the present invention there is provided a process for the preparation of a dihydropyran-2-one of the Formula (2):

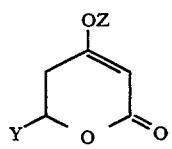

Formula (2)

by reduction of a pyran-2-one of the Formula (3):

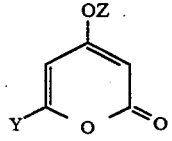

Formula (3)

wherein Y and Z are as hereinbefore defined.

The process may be performed by chemical reduction, where the pyran-2-one of Formula (3) preferably in a liquid medium, is reacted with hydrogen in the presence of a catalyst. The liquid medium is preferably an organic liquid and especially an alkanol such as ethanol, or propanol or an ester such as ethylacetate. Suitable catalysts are metal catalysts preferably where the metal is from Group VIII of the Periodic Table. The catalyst is preferably a finely divided metal or metal supported on a carbon or aluminium oxide support and is optionally modified by pre-treatment before use in the process. The catalyst is preferably palladium on carbon with a metal loading of from 0.5 to 10% by weight preferably from 1 to 5% by weight. The process is preferably performed at a temperature from 0° C. to 80° C., preferably from 15° C. to 50° C., especially from 20° C. to 30° C. The process is preferably performed at a pressure from $1 \times 10^4$ Pa to $1 \times 10^7$ Pa, more preferably from $1 \times 10^5$ Pa to $1 \times 10^7$ Pa. The process is preferably continued until all the starting material is consumed. The product may be isolated by removing the catalyst by filtration and evaporation of the liquid medium. The product may be purified by any convenient means such as distillation or crystallisation.

According to a further feature of the present invention there is provided a process for the resolution of dihydropyran-2-ones of the Formula (2):

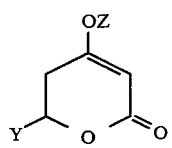

Formula (2)

which comprises a selective reaction of one enantiomer with a reagent catalysed by a hydrolase enzyme whereby the enantiomer is preferentially converted into a distinct chemical species from the other enantiomer so that it is susceptible of separation by an appropriate chemical or physical separation process, wherein:

Y and Z are as hereinbefore defined.

The conditions for trans-esterification, esterification and hydrolysis reactions described above for the resolution of compounds of Formula (1) are applicable to the resolution of compounds of Formula (2); although the especially preferred enzymes used for the resolution of the compounds of Formula (2) are Pseudomonas fluorescens lipase from Biocatalysts or Fluka Chemie, Chromobacterium viscosum lipase from Biocatalysts, Candida cylindracae from Biocatalysts, Fluka Chemie or Sigma, Mucor miehi from Biocatalysts or Fluka Chemie and Lipoprotein lipase from Boehringer Mannheim or Fluka Chemie. The process may be illustrated by the following schemes whereby a racemate of Formula (2) may be resolved:

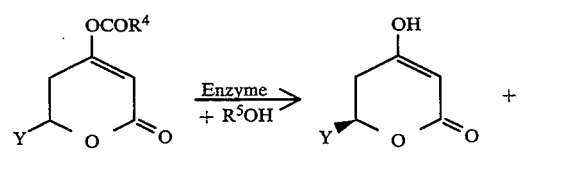

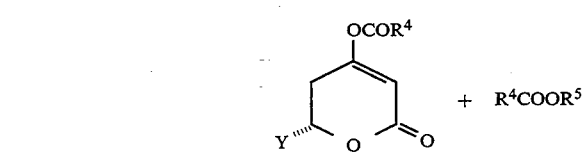

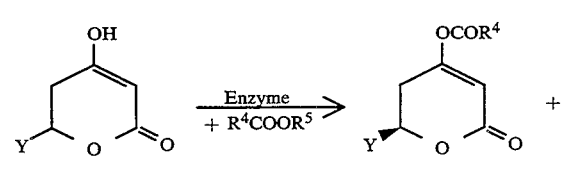

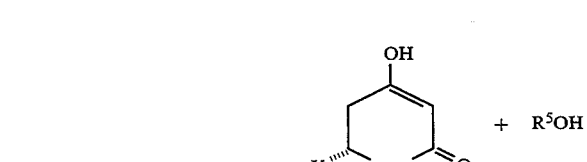

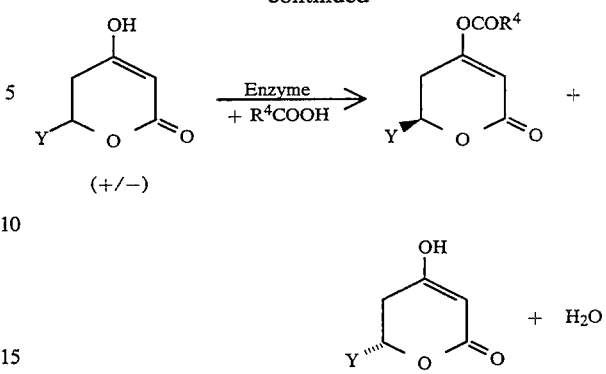

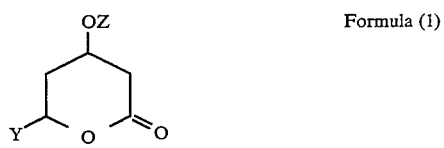

The products depicted in each of these schemes are distinct chemical species and may be separated by appropriate conventional separation methods such as solvent extraction, chromatography or crystallisation.

According to a further feature of the present invention there is provided a process for the preparation of a tetrahydropyran-2-one of the Formula (1):

Formula (1)

by reduction of a pyran-2-one of the Formula (3):

Formula (3)

wherein Y and Z are as hereinbefore defined.

The process may be performed by chemical reduction where the pyran-2-one of Formula (3) is reacted in a liquid medium with hydrogen in the presence of a catalyst. The liquid medium is preferably an organic liquid and more preferably an alkanol such as methanol, ethanol, n-propanol or n-butanol or an ester such as ethyl acetate. Alternatively, the liquid medium may be water or a mixture of water and alkanol such as water-/ethanol. Suitable catalysts are metal catalysts preferably those where the metal is from Group VIII of the Periodic Table. The catalyst is preferably a finely divided metal or a metal carried on a support such as carbon, more preferably Raney Nickel. The process is preferably performed at a temperature from 20° C. to 130° C. and more preferably from 50° C. to 100° C. The process may be conveniently carried out at the boiling point of the liquid medium. The process is performed at a pressure from $1 \times 10^4$ Pa to $1 \times 10^6$ Pa, preferably from $5 \times 10^4$ Pa to $5 \times 10^5$ Pa and especially from $8 \times 10^4$ Pa to $2 \times 10^5$ Pa. The process is preferably continued until substantially all the starting material is consumed. The product is isolated by removing the catalyst by filtration and evaporation of the liquid medium. The product is purified by any convenient means such as chromatography, distillation or crystallisation.

The hydrogenation of the pyran-2-one of Formula (3) to the tetrahydropyran-2-one of Formula (1) may be carried out in two stages without isolation of the intermediate dihydropyran-2-one of Formula (2), the first stage in the presence of a more selective catalyst, such as palladium on carbon and the second stage in the presence of a less selective catalyst, such as Raney nickel.

According to the a further feature of present invention there is provided a process for the preparation of a compound of the Formula (13):

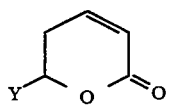

Formula (13)

by the elimination of ZOH from a compound of Formula (1):

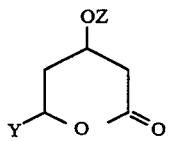

Formula (1)

wherein:

Y and Z are as hereinbefore defined.

A particular utility, which forms a further feature of the present invention, of the compounds of Formula (13) is that they permit the synthesis of trans-isomers of compounds of Formula (1) from the corresponding cis-isomers or from the corresponding cis/trans-mixtures for example:

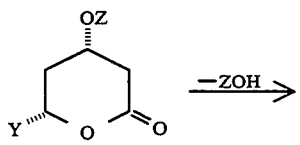

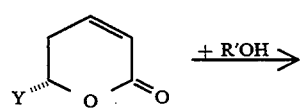

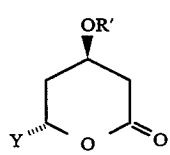

wherein:

R' is any of the groups hereinbefore defined for Z; and

Y is as hereinbefore defined.

For compounds of Formula (1) in which Z is —H the process may be performed by dehydrating the compound of Formula (1) in a liquid medium in the presence of a dehydration catalyst. The liquid medium is preferably an organic liquid, more preferably an aromatic hydrocarbon such as toluene or xylene. Suitable dehydration catalysts are sulphonic acids preferably aromatic sulphonic acids such as p-toluenesulphonic acid. The process is preferably performed at a temperature from 20° C. to 150° C., more preferably from 50° C. to 150° C. and especially at the boiling point of the liquid medium.

The reaction is continued until substantially all the starting material is consumed. After washing to remove the catalyst the product is isolated by evaporation of the liquid medium and is purified by any convenient means such as crystallisation, solvent extraction or chromatography.

For compounds of Formula (1) in which Z is for example —SO.OR$^3$, —(CO)OR$^3$, —CO.R$^3$ or —PO.(OR$^3$)$_2$ the process may be performed by eliminating HOSO$_2$R$^3$, HO(CO)OR$^3$, HOCO.R$^3$ or HOPO.(OR$^3$)$_2$ respectively from the compound of Formula (1) by reaction with a base in a liquid medium. Suitable bases are organic nitrogen bases such as triethylamine, 1,8-diazabicyclo[5.4.0]undec-7-ene (DBU) and 1,5-diazabicyclo[4.3.0]non-5-ene (DBN), metal alkoxides, preferably alkali metal alkoxides such as sodium ethoxide or potassium t-butoxide or inorganic bases such as sodium carbonate. The liquid medium is preferably an organic liquid, more preferably an a halocarbon such as dichloromethane, an aromatic hydrocarbon such as toluene or an anhydrous dipolar aprotic liquid such as dimethylformamide (DMF) and dimethylsulphoxide (DMSO). The process may optionally be performed in the presence of a phase transfer catalyst. Suitable phase transfer catalysts are alkyl ammonium halides such as tetrabutylammonium bromide and tetramethylammonium bromide or chloride. The process is preferably performed at a temperature from 20° C. to 200° C., more preferably at 30° C. to 100° C. The reaction is continued until substantially all.the starting material is consumed. After treatment to remove residual base, the product may be isolated by evaporation of the liquid medium and purified as above.

Elimination of ZOH from an individual enantiomer of Formula (1) by the above process produces a single optical isomer of Formula (13).

In compounds of Formula (1) in which Z is —H the 4-hydroxy group may be converted to a sulphonate ester group by reaction with the corresponding sulphonyl chloride, such as 4-toluenesulphonyl chloride or methanesulphonyl chloride in the presence of pyridine.

According to a further feature of the present invention there is provided a process for the preparation of a pyran-2-one of the Formula (3):

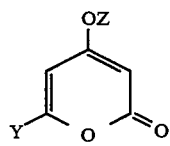

Formula (3)

wherein:

Y is hydrocarbyl substituted by —CN, —OR, —SR, —N$_3$, —PO.(OR$^3$)$_2$, —PO.(R$^3$)$_2$ or —P(R$^3$)$_3$+X$^-$ in which R, R$^3$ and X$^-$ are as hereinbefore defined; and Z is as hereinbefore defined by reaction of a pyran-2-one of the Formula (4):

Formula (4)

wherein:

$Y^1$ is hydrocarbyl substituted by halogen; and
Z is as hereinbefore defined
with a compound of Formula MQ in which M is —H or metal; and Q is —CN, —$N_3$, —OR, —SR, —$CS_3$ in which R is as hereinbefore defined, or in which MQ is $P(OR^3)_3$, $(R^3)_2POR^3$ or $P(R^3)_3$ in which $R^3$ is as hereinbefore defined.

In pyran-2-ones of Formula (4) $Y^1$ is preferably $C_{1-3}$-hydrocarbyl, especially a $C_{1-2}$-alkyl or $C_{2-3}$-alkenyl and is preferably substituted by —Cl, —Br or —I, especially —Br.

The pyran-2-one of Formula (3) in which Y is hydrocarbyl substituted by —OH may be formed by hydrolysis of the pyran-2-one of Formula (4) in a liquid medium. The liquid medium is preferably aqueous i.e. MQ is $H_2O$ containing an inorganic base such as sodium hydroxide. The conversion of a pyran-2-one of Formula (4) to a pyran-2-one of Formula (3) in which Y is hydrocarbyl substituted by —OH may also be effected by treatment of the pyran-2-one of Formula (3) with silver nitrate in aqueous or alcoholic media. The pyran-2-one of Formula (3) in which Y is hydrocarbyl substituted by —OR and R is optionally substituted alkyl, optionally substituted alkenyl or optionally substituted phenyl may be formed by reaction of the pyran-2-one of Formula (4) with a compound ROH in the presence of an inorganic base such as potassium hydroxide under non-aqueous conditions.

In compounds of Formula (4) Y is preferably —CN, —$N_3$, —$OCH_2Ph$, —$SCH_2Ph$, —SH, —OH, —$PO(OPh)_2$, —$PO.(OEt)_2$, —$PO(Ph)_2$, —$PPh_3^+Br^-$ or —$P(CH_2Ph)_3^+Br^-$.

M is preferably —H, Li, Na or K, Q is preferably —CN, —$N_3$, —$OCH_2Ph$, —$SCH_2Ph$, —$CS_3$ or —OH or MQ is preferably $P(OPh)_3$, $P(OEt)_3$, $Ph_2P(OPh)$, $PPh_3$ or $P(CH_2Ph)_3$. These processes are preferably carried out at a temperature from 25° C. to 150° C., more preferably 40° C. to 100° C. and may be conveniently carried out at the reflux temperature of the liquid medium. The process is continued until substantially all the starting material is consumed. The product may be isolated by evaporation of the liquid medium and purified by any convenient means such as solvent extraction, column chromatography and crystallisation.

The pyran-2-one of Formula (3) in which Y is hydrocarbyl substituted by —CN may be formed by cyanation of a pyran-2-one of Formula (4) in a liquid medium with a cyanide. The liquid medium is preferably (a) an organic liquid, especially an aromatic hydrocarbon such as toluene or an alkanol such as ethanol or methanol or (b) water or (c) a dipolar aprotic solvent such as dimethylformamide. Mixtures of liquid media may be used and where mixtures of two liquid media which are partly or substantially immiscible are used, a phase transfer catalyst may also be used. Suitable phase transfer catalysts are tetraalkylammonium halides, such as tetrabutylammonium bromide. Phase transfer catalysts may also be used when a liquid medium in which the cyanide is substantially insoluble is used. The cyanide is preferably an inorganic cyanide such as sodium or potassium cyanide. An especially preferred liquid medium for cyanation is (a) a mixture of aqueous potassium cyanide, toluene and a phase transfer catalyst such as tetrabutylammonium bromide, or (b) a mixture of sodium cyanide, ethanol and water or (c) a mixture of sodium cyanide and methanol or (d) a mixture of sodium cyanide and anhydrous dimethylformamide. This process is preferably carried out at a temperature from 0° C. to 100° C., more preferably from 10° C. to 40° C. The process is continued until substantially all the starting material is consumed. The product may be isolated, after removing any solids by filtration, by evaporation of the liquid medium to leave a residue. The residue may be dissolved in a water-immiscible organic liquid preferably a haloalkane such as dichloromethane, a ketone such as methyl isobutyl ketone or an ester such as ethyl acetate and washed with water to remove residual inorganic material. Separation of the organic layer from the water followed by evaporation of the organic liquid gives the pyran-2-one of Formula (3) in which Y is hydrocarbyl substituted by —CN which may be purified by any convenient means such as crystallisation or column chromatography.

The pyran-2-one of Formula (3) in which Y is hydrocarbyl substituted by —CN may be hydrolysed to the corresponding pyran-2-one of Formula (3) in which Y is hydrocarbyl substituted by —$CONH_2$ in an acidic medium, preferably in an aqueous acid such as sulphuric, acetic or hydrobromic at a temperature from 0° C. to 120° C.

The pyran-2-one of Formula (3) in which Y is hydrocarbyl substituted by —CN may be hydrolysed to the corresponding pyran-2-one of Formula (3) in which Y is hydrocarbyl substituted by —COOH under more forcing conditions i.e. stronger acid solution and/or higher temperatures. The pyran-2-one of Formula (3) in which Y is hydrocarbyl substituted by —COOH may be converted by reaction with an amine of formula $(R^3)_2NH$, in which $R^3$ is as hereinbefore defined, in the presence of a mild dehydrating agent in a liquid medium. The mild dehydrating agent is preferably a carbodiimide such as dicyclohexylcarbodiimide and the liquid medium is preferably a haloalkane such as tetrachloro-, trichloro- or dichloromethane or an ether such as tetrahydrofuran or diethylether or an alkyl cyanide such as acetonitrile. The reaction is preferably carried out at a temperature from —20° to 50° C. and more preferably from —10° to 25° C.

The pyran-2-one of Formula (3) in which Y is hydrocarbyl substituted by —SR may be formed by reaction of a pyran-2-one of Formula (4) with a compound of formula MSR in a liquid medium. The liquid medium is preferably an organic liquid, more preferably an alkanol such as ethanol or methanol. The liquid medium is preferably deoxygenated for example by purging with an inert gas such as argon or nitrogen. The compound of formula MSR is preferably an alkyl mercaptide such as sodium methylmercaptide, sodium propylmercaptide or potassium ethylmercaptide or is a thiophenate such as sodium or potassium thiophenate. The alkylmercaptide may be prepared by addition of sodium methoxide in methanol to the corresponding methyl mercaptan, similarly the thiophenate may be prepared by addition of sodium ethoxide in ethanol to thiophenol. The present process is preferably performed at a temperature from 0° C. to 80° C., more preferably from 10° C. to 30° C. The reaction is continued until substantially all the starting material has been consumed. The product is isolated by evaporating the liquid medium and filtering or ion exchange to remove potassium or sodium halide. The product may be purified by any convenient means such as column chromatography or crystallisation.

The pyran-2-one of Formula (3) in which Y is hydrocarbyl substituted by —SH may be formed by thiolating a compound of Formula (4) in a liquid medium. The liquid medium is preferably water or an organic liquid, especially an alkanol such as methanol or ethanol or more preferably a mixture of an alkanol and water. The liquid medium is preferably deoxygenated before use for example by purging with an inert gas such as helium. The thiolating agent is preferably sodium trithiocarbonate. The process is preferably carried out at a temperature from −20° C. to 60° C., more preferably from −5° C. to 20° C. The process is preferably carried out under an inert gas atmosphere. Suitable inert gases are argon, helium and nitrogen. The reaction is continued until substantially all the starting material is consumed. The product may be isolated by acidifying the reaction mixture followed by extraction with ether, evaporating the ether and purifying by any convenient means such as column distilling the residue under reduced pressure chromatography or crystallisation but taking care to exclude oxygen and thus prevent oxidation of the product.

The pyran-2-one of Formula (3) in which Y is hydrocarbyl substituted by —PO.(OR$^3$)$_2$, —PO.(R$^3$)$_2$ or P+(R$^3$)$_3$X− may be prepared by reacting a pyran-2-one of Formula (4) with a phosphite of Formula P(OR$^3$)$_3$ or a phosphine of Formula (R$^3$)$_2$POR$^3$ or P(R$^3$)$_3$ respectively in , which X and each R$^3$ independently is as hereinbefore defined, in a liquid medium preferably an organic liquid medium more preferably in an aromatic hydrocarbon such as toluene at a temperature from 50° C. to 150° C. more preferably at 80° C. to 120° C.

The pyran-2-one of Formula (3) in which Y is hydrocarbyl substituted by —OZ may be formed by reaction of the corresponding hydroxy compound with a compound of formula Z$^1$Cl wherein Z$^1$ is as hereinbefore defined except where Z is NO$_2$ and tetrahydropyran-2-yl. Pyran-2-ones of Formula (3) in which Y is hydrocarbyl substituted by —OZ$^1$ and Z$^1$ is NO$_2$ may be prepared by reacting the corresponding compound in which Z$^1$ is mesyl and a tetraalkylammonium nitrate. Pyran-2-ones of Formula (3) in which Y is hydrocarbyl substituted by —OZ$^1$ and Z$^1$ is tetrahydropyran-2-yl may be prepared by reaction of the corresponding compound in which Z$^1$ is hydroxy with dihydropyran. Further details of reactions to protect hydroxyl groups are described in 'Protective Groups in Organic Synthesis', T. W. Greene and P. G. M. Wuts, published by Wiley & Sons 2nd Edition (1991).

The pyran-2-ones of Formula (3) in which Y is hydrocarbyl substituted by —CN, —OR, —CON(R)$_2$, —SR, —PO(OR$^3$)$_2$, —PO(R$^3$)$_2$ or P+(R$^3$)$_3$X− in which each R and each R$^3$ independently is as hereinbefore defined may be reduced to the corresponding dihydropyran-2-one or tetrahydropyran-2-one under the conditions described above.

The pyran-2-ones of Formula (3) in which Z is —H may also be prepared by the reaction of an acid chloride of formula YCOCl, in which Y is as hereinbefore defined, with 2 equivalents of keten. In this reaction an intermediate substituted dioxopentanoic acid chloride is formed which is cyclised to form the compound of Formula (3).

The pyran-2-ones of Formula (3) in which Z is —H may also be prepared by the self-condensation of two equivalents of a beta-keto ester of the formula YCOCH$_2$CO$_2$Et, in which Y is as hereinbefore defined, in a liquid medium such as chloroform in the presence of phosphorus pentoxide, (see Izv. Akad. Nauk. SSR, Ser. Khim. (1982) 1657) followed by deacylation to remove a —COY group from the 3-position.

According to a further feature of the present invention there is provided a process for the preparation of a pyran-2-one of the Formula (4):

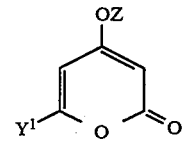

Formula (4)

by removal of the group W from a pyran-2-one of the Formula (5):

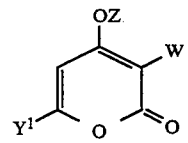

Formula (5)

wherein:
W is —COT in which T is an optionally substituted hydrocarbon group —CX$_3$, —CHX$_2$, —CH$_2$X in which X is halogen;
Y$^1$ and Z are as hereinbefore defined.

In pyran-2-ones of Formula (5) W is preferably —COC$_{1-2}$-alkyl or —COC$_2$-alkenyl each of which may be optionally substituted by halogen, —CN, —OR$^6$ or SR$^6$ in which R$^6$ is —H, C$_{1-6}$-alkyl, C$_{2-12}$-alkenyl or phenyl, W is more preferably —COCH$_3$, —COCH$_2$Cl, —COCH$_2$Br, —COCHBr$_2$ or —COCHCl$_2$ and Y$^1$ is preferably hydrocarbyl substituted by —Br.

The present process may be performed by heating the pyran-2-one of Formula (5) in a liquid medium in the presence of an acid. The acid is preferably an inorganic acid, more preferably H$_2$SO$_4$. The process is preferably performed at a temperature from 50° C. to 200° C., more preferably at from 80° C. to 150° C. and especially at from 80° C. to 135° C. The process is preferably continued until all the starting material is consumed. The product may be isolated by neutralising the reaction mixture and extracting with a solvent and evaporating the solvent. The product may be purified by any convenient method such as distillation or crystallisation.

The removal of W may be conveniently carried out at any stage in the overall process, i.e. if a pyran-2-one of Formula (3) or (4) or (6) below carries a group W in the 3-position this may be removed under similar conditions to those described above.

According to a further feature of the present invention there is provided a process for the preparation of a pyran-2-one of the Formula (5):

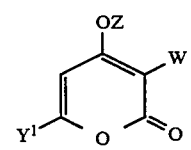

Formula (5)

by halogenation of a pyran-2-one of the Formula (6):

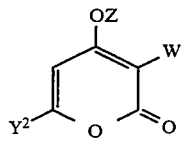

Formula (6)

wherein:
Y$^1$, W and Z are as hereinbefore defined; and
Y$^2$ is unsubstituted hydrocarbyl.

In compounds of Formula (6) Y$^2$ is preferably C$_{1-3}$-hydrocarbyl, more preferably C$_{1-2}$-alkyl or C$_{2-3}$-alkenyl, and especially methyl and W is preferably —COCH$_3$.

The halogenation of a pyran-2-one of Formula (6) may be performed in a liquid medium with a halogenating agent, optionally in the presence of ultraviolet light and preferably in the presence of a free radical initiator such as an organic peroxide.

The liquid medium is preferably an organic liquid which either does not itself undergo halogenation under the reaction conditions or which is already fully halogenated. The organic liquid is preferably a haloalkane such as tetrachloromethane or hexachloroethane. The halogenating agent is preferably an N-halosuccinimide such as N-chlorosuccinimide for chlorination, N-bromosuccinimide for bromination.

The free radical initiator is preferably an aromatic peroxide such as benzoyl peroxide or an aliphatic peroxide such as t-butyl hydroperoxide.

The process is preferably carried out at a temperature from 0° C. to 100° C. and more preferably from 30° C. to 80° C. The reaction is continued until substantially all the starting material has been consumed. The product is isolated by evaporation of the liquid medium and purified by any convenient means such as solvent extraction, distillation or column chromatography.

Pyran-2-ones of Formula (5) where X is —I may also be prepared from pyran-2-ones of Formula (5) where X is —Br by halogen exchange in a liquid medium with iodide optionally in the presence of a phase transfer catalyst. The phase transfer catalyst is preferably a tetraalkyl ammonium halide such as tetrabutylammonium bromide. The liquid medium is preferably an organic liquid, more preferably a ketone such as acetone or methylethylketone or a lower alkanol such as ethanol or isopropanol. The iodide is preferably an inorganic iodide such as potassium or sodium iodide. This process forms a further aspect of the present invention.

According to a further feature of the present invention there is provided a resolved isomer of the Formula (1):

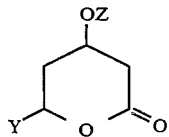

Formula (1)

wherein:
Z is —H or a protecting group; and
Y is C$_{1-3}$-hydrocarbyl optionally substituted by —CN, —Cl, —Br, —PO(R$^3$)$_2$, —PO(OR$^3$)$_2$, —F, —I, azide, —OR, —SR, —P(R$^3$)$_3^+$X$^-$ and —OZ$^1$ in which R, R$^3$, X and Z$^1$ are as hereinbefore defined except for the compounds (4R,6S) 4-hydroxy-6-benzyloxymethyl-tetrahydropyran-2-one,
(4S,6S) 4-hydroxy-6-benzyloxymethyl-tetrahydropyran-2-one,
(4R,6S) 4-hydroxy-6-hydroxymethyl-tetrahydropyran-2-one,
(4R,6S) 4-hydroxy-6-(t-butyldiphenylsilyloxymethyl)-tetrahydropyran-2-one,
(4S,6S) 4-hydroxy-6-(t-butyldiphenylsilyloxymethyl)-tetrahydropyran-2-one,
(4R,6S) 4-(t-butyldimethylsilyloxy)-6-hydroxymethyl-tetrahydropyran-2-one,
(4S,6S) 4-(t-butyldimethylsilyloxy)-6-hydroxymethyl-tetrahydropyran-2-one,
(4R,6R) 4-hydroxy-6-(triisopropylsilyloxymethyl)-tetrahydropyran-2-one,
(4S,6R) 4-hydroxy-6-(triisopropylsilyloxymethyl)-tetrahydropyran-2-one,
(4S,6S) 4-benzyloxy-6-benzyloxymethyl-tetrahydropyran-2-one,
(4R,6S) 4-(t-butyldimethylsilyloxy)-6-benzyloxymethyl-tetrahydropyran-2-one,
(4S,6S) 4-(t-butyldiphenylsilyloxy)-6-benzyloxymethyl-tetrahydropyran-2-one,
(4R,6S) 4-(t-butyldiphenylsilyloxy)-6-tosyloxymethyl-tetrahydropyran-2-one,
(4S,6S) 4-(t-butyldimethylsilyoxy)-6-t-butyldimethylsilyloxymethyl-tetrahydropyran-2-one,
(4R,6S) 4-(t-butyldimethylsilyloxy)-6-tosyloxymethyl-tetrahydropyran-2-one,
(4S,6S) 4-(t-butyldimethylsilyloxy)-6-tosyloxymethyl-tetrahydropyran-2-one,
(4R,6S) acetyloxy-6-acetyloxymethyl-tetrahydropyran-2-one,
(4R,6S) 4-hydroxy-6-iodomethyl-tetrahydropyran-2-one,
(4R,6R) 4-hydroxy-6-iodomethyl-tetrahydropyran-2-one,
(4R,6S) 4-(t-butyldimethylsilyloxy)-6-iodomethyl-tetrahydropyran-2-one,
(4R,6R) 4-(t-butyldimethylsilyloxy)-6-iodomethyl-tetrahydropyran-2-one,
(4R,6S) 4-(triisopropylsilyloxy)-6-iodomethyl-tetrahydropyran-2-one,
(4R,6R) 4-(triisopropylsilyloxy)-6-iodomethyl-tetrahydropyran-2-one,
(4R,6S) 4-(t-butyldiphenylsilyloxy)-6-iodomethyl-tetrahydropyran-2-one,
(4S,6S) 4-(t-butyldiphenylsilyloxy)-6-iodomethyl-tetrahydropyran-2-one,
(4R,6R) 4-(t-butyldiphenylsilyloxy)-6-iodomethyl-tetrahydropyran-2-one,
(4S,6R) 4-(t-butyldiphenylsilyloxy)-6-iodomethyl-tetrahydropyran-2-one,
(4S,6S) 4-hydroxy-6-chloromethyl-tetrahydropyran-2-one,
(4R,6S) 4-hydroxy-6-methyl-tetrahydropyran-2-one,
(4R,6R ) 4-hydroxy-6-methyl-tetrahydropyran-2-one,
(4S,6R) 4-hydroxy-6-methyl-tetrahydropyran-2-one.

A preferred sub-group of tetrahydropyran-2-ones of Formula (1) are those in which
Z is —NO$_2$, —PO(OR$^3$)$_2$, —CO.R$^3$, —SO.OR$^3$ and —CO.OR$^3$ in which R$^3$ is C$_{1-4}$-alkyl, phenyl or benzyl; and
Y is —CH$_3$, —CH$_2$CN, —CH$_2$Cl, —CH$_2$Br, —CH$_2$I, —CHCl$_2$, —CHBr$_2$, —CBr$_3$, —CCl$_3$, —CH$_2$OR in which R is —H, C$_{1-6}$-alkyl, C$_{2-6}$-alkenyl or phenyl, —C$_2$H$_4$N$_3$, —CH$_2$SR$^3$, —CH$_2$P(R$^3$)$_3^+$X$^-$, —CH- $_2PO(OR^3)_2$, —$CH_2PO(R^3)_2$ in which $R^3$ is $C_{1-4}$-alkyl, phenyl or benzyl and X is Cl, Br or I, and —$CH_2OZ^1$ in which $Z^1$ is —H, $SiPh_2Bu^t$, —$SiMe_2$-$Bu^t$, —$Si(iPr)_3$, tetrahydropyran-2-yl methoxymethyl, methoxyethoxymethyl, —$SiMe_3$, —$SiEt_3$ and —$SiPh_3$.

A further preferred sub-group of tetrahydropyran-2-ones of Formula (1) are those in which:

Z is —H, —$NO_2$, —$PO(OR^3)_2$, —$CO.R^3$, —$SO.OR^3$ and —$CO.OR^3$ in which each $R^3$ independently is $C_{1-4}$-alky, phenyl or benzyl; and Y is —$CH_2CN$, —$CH_2Br$, —$CHCl_2$, —$CHBr_2$, —$CBr_3$, —$CCl_3$, —$C_2H_4N_3$, —$CH_2SR^3$, —$CH_2P(R^3)_3{}^{3O}X^-$, —$PO.(OR^3)_2$, —$PO.(R^3)_2$ in which $R^3$ is $C_{1-4}$-alkyl or phenyl and X is —Cl, —Br or —I, —$CH_2OR$ in which R is $C_{1-6}$-alkenyl or phenyl, and —$CH_2OZ^1$ in which $Z^1$ is —$SiBu^t$-$Me_2$.

Especially preferred tetrahydropyran-2-ones of Formula (1) are those in which Z is H, —$CO.R^3$ in which $R^3$ is $C_{1-3}$-alkyl, Y is —$CH_2OSiBu^tMe_2$, —$CH_2CN$, —$CH_2Br$, —$C_2H_4N_3$, $CH_2Cl$, —$CH_2OCH_2Ph$, —$CH_2I$.

A preferred resolved tetrahydropyran-2-one isomer of Formula (1) is of Formula (7):

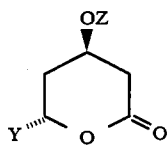

Formula (7)

wherein:

Z is —H or a protecting group; and

Y is $C_{1-3}$-hydrocarbyl optionally substituted by —CN, —Cl, —Br, —F, —I, azide, —OR, —SR, —$P(R^3)_3{}^+X^-$, —$PO(OR^3)_2$, $PO(R^3)_2$ and —$OZ^1$ in which R, $R^3$, X and $Z^1$ are as hereinbefore defined except for the compounds (4R,6S) 4-hydroxy-6-benzyloxymethyl-tetrahydropyran-2-one, (4R,6S) 4-hydroxy-6-hydroxymethyl-tetrahydropyran-2-one, (4R,6S) 4-hydroxy-6-(t-butyldiphenylsilyloxymethyl)-tetrahydropyran-2-one, (4R,6S) 4-(t-butyldimethylsilyloxy)-6-hydroxymethyl-tetrahydropyran-2-one, (4R,6S) 4-(t-butyldimethylsilyloxy)-6-benzyloxymethyl-tetrahydropyran-2-one, (4R,6S) 4-(t-butyldiphenylsilyloxy)-6-tosyloxymethyl-tetrahydropyran-2-one, (4R,6S) 4-(t-butyldimethylsilyoxy)-6-tosyloxymethyl-tetrahydropyran-2-one, (4R,6S) 4-acetyloxy-6-acetyloxymethyl-tetrahydropyran-2-one, (4R,6S) 4-hydroxy-6-iodomethyl-tetrahydropyran-2-one, (4R,6S) 4-(t-butyldimethylsilyloxy)-6-iodomethyl-tetrahydropyran-2-one, (4R,6S) 4-(triisopropylsilyloxy)-6-iodomethyl-tetrahydropyran-2-one, (4R,6S) 4-(t-butyldiphenylsilyloxy)-6-iodomethyl-tetrahydropyran-2-one, (4R,6S) 4-hydroxy-6-methyl-tetrahydropyran-2-one.

A further preferred resolved tetrahydropyran-2-one isomer of Formula (1) is of Formula (8):

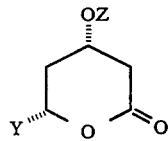

Formula (8)

wherein:

Z is —H or a protecting group; and

Y is $C_{1-3}$-hydrocarbyl optionally substituted by —CN, —Cl, —Br, —F, —I, azide, —OR, —SR, —$P(R^3)_3{}^+X^-$, —$PO(OR^3)_2$, —$PO(R^3)_2$ and —$OZ^1$ in which R, $R^3$, X and $Z^1$ are as hereinbefore defined except for the compounds (4S,6S) 4-hydroxy-6-benzyloxymethyl-tetrahydropyran-2-one, (4S,6S) 4-hydroxy-6-(t-butyldiphenylsilyloxymethyl)-tetrahydropyran-2- one, (4S,6S) 4-(t-butyldimethylsilyloxy)-6-hydroxymethyl-tetrahydropyran-2-one, (4S,6S) 4-benzyloxy-6-benzyloxymethyl-tetrahydropyran-2-one, (4S,6S) 4-(t-butyldiphenylsilyloxy)-6-benzyloxymethyl-tetrahydropyran-2- one, (4S,6S) 4-(t-butyldimethylsilyoxy)-6-t-butyldimethylsilyloxymethyl-tetrahydropyran-2-one, (4S,6S) 4-(t-butyldimethylsilyloxy)-6-tosyloxymethyl-tetrahydropyran-2-one, (4S,6S) 4-(t-butyldiphenylsilyloxy)-6-iodomethyl-tetrahydropyran-2-one, (4S,6S) 4-hydroxy-6-chloromethyl-tetrahydropyran-2-one.

A further preferred resolved tetrahydropyran-2-one isomer of Formula (1) is of Formula (9):

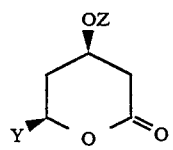

Formula (9)

wherein:

Z is —H or a protecting group; and

Y is $C_{1-3}$-hydrocarbyl optionally substituted by —CN, —Cl, —Br, —F, —I, azide, —OR, —SR, —$P(R^3)_3{}^+X^-$, —$PO(OR^3)_2$, —$PO(R^3)_2$ and —$OZ^1$ in which R, $R^3$, X and $Z^1$ are as hereinbefore defined except for the compounds (4R,6R) 4-hydroxy-6-(triisopropylsilyloxymethyl)-tetrahydropyran-2-one, (4R,6R) 4-hydroxy-6-iodomethyl-tetrahydropyran-2-one, (4R,6R) 4-(t-butyldimethylsilyloxy)-6-iodomethyl-tetrahydropyran-2-one, (4R,6R) 4-(triisopropylsilyloxy)-6-iodomethyl-tetrahydropyran-2-one, (4R,6R) 4-(t-butyldiphenylsilyloxy)-6-iodomethyl-tetrahydropyran-2-one, (4R,6R) 4-hydroxy-6-methyl-tetrahydropyran-2-one.

A further preferred resolved tetrahydropyran-2-one isomer of Formula (1) is of Formula (10):

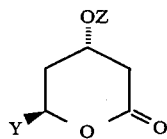

Formula (10)

wherein:

Z is —H or a protecting group; and

Y is $C_{1-3}$-hydrocarbyl optionally substituted by —CN, —Cl, —Br, —F, —I, azide, —OR, —SR, —P($R^3$)$_3$+X−, —PO(O$R^3$)$_2$, —PO($R^3$)$_2$ and —O$Z^1$ in which R, $R^3$, X and $Z^1$ are as hereinbefore defined except for the compounds (4S,6R) 4-hydroxy-6-(triisopropylsilyloxymethyl)-tetrahydropyran-2-one, (4S,6R) 4-(t-butyldiphenylsilyloxy)-6-iodomethyl-tetrahydropyran-2-one, (4S,6R) 4-hydroxy-6-methyl-tetrahydropyran-2-one.

Further preferred resolved tetrahydropyran-2-one isomers of Formulae (7), (8), (9) and (10) are those in which Z is —H, —NO$_2$, —PO(O$R^3$)$_2$, —SO.O$R^3$ and —CO.O$R^3$ in which each $R^3$ independently is $C_{1-4}$-alkyl, phenyl or benzyl; and Y is $C_{1-3}$-hydrocarbyl substituted by —CN, —Br, —F, azide, —P($R^3$)$_3$+X−, —PO(O$R^3$)$_2$, —PO($R^3$)$_2$, —O$Z^1$ in which each $R^3$ independently is $C_{1-4}$-alkyl, phenyl or benzyl and $Z^1$ is tetrahydro pyran-2-yl, alkoxyalkyl, alkoxyalkoxyalkyl, triarylmethyl, —NO$_2$, —PO(O$R^3$)$_2$, —CO$R^3$, —SO.O$R^3$ and —CO.O$R^3$ in which each $R^3$ independently is $C_{1-4}$-alkyl, phenyl or benzyl.

Further preferred resolved tetrahydropyran-2-one isomers of Formulae (7), (8), (9) and (10) are those in which Z is —NO$_2$, —CO.$R^3$, —PO(O$R^3$)$_2$, —SO.O$R^3$ and —CO.O$R^3$ in which each $R^3$ independently is $C_{1-4}$-alkyl, phenyl or benzyl; Y is $C_{1-3}$-hydrocarbyl optionally substituted by —CN, —Cl, —Br, —F, —I, azide, —OR, —SR, —P($R^3$)$_3$+X−, —PO(O$R^3$)$_2$, —PO(O$R^3$), —O$Z^1$ in which R is H, $C_{1-4}$-alkyl or phenyl, each $R^3$ independently is $C_{1-4}$-alkyl, phenyl or benzyl; and $Z^1$ is tetrahydro pyran-2-yl, alkoxyalkyl, alkoxyalkoxyalkyl, phenylalkyl, triarylmethyl, —NO$_2$, —PO.(O$R^3$)$_2$, —SO.O$R^3$, —CO.O$R^3$ and Si($R^3$)$_3$ in which each $R^3$ independently is $C_{1-4}$-alkyl, phenyl or benzyl.

The compounds of Formula (1) have at least two chiral centres, on the carbon atoms at the 4- and 6-positions of the pyran ring and the combinations of isomers in any compound will be determined by the preparative process used.

Additional chiral centres may be present in compounds of Formula (1) where the groups represented by Y and Z also contain a chiral centre and such additional chiral centres give the possibility of further isomers in the mixture.

The compound of Formula (1) may exist as two racemates, one racemate is a mixture of the compound of Formula (7) and the compound of Formula (10) wherein Y and Z are the same in each compound in the racemate; the other racemate is a mixture of the compound of Formula (8) and the compound of Formula (9) wherein Y and Z are the same in each compound.

According to a further feature of the present invention there is provided a racemate of the compounds of Formulae (7) and (10) wherein Z is —H or a protecting group susceptible of reaction with the reagent under the influence of the enzyme; and Y is $C_{1-3}$-hydrocarbyl optionally substituted by —CN, —Cl, —Br, —F, —I, azide, —OR, —SR, —P($R^3$)$_3$+X−, —PO(O$R^3$)$_2$, —PO($R^3$)$_2$ and —O$Z^1$ in which R, $R^3$, X and $Z^1$ are as hereinbefore defined except for trans(±)4-acetyloxy-6-acetyloxymethyl tetrahydropyran-2-one.

According to a further feature of the present invention there is provided a racemate of compounds of the Formulae (8) and (9) wherein Z is —H or a protecting group susceptible of reaction with the reagent under the influence of the enzyme; and Y is $C_{1-3}$-hydrocarbyl optionally substituted by —CN, —Cl, —Br, —F, —I, azide, —OR, —SR, —P($R^3$)$_3$+X−, —PO(O$R^3$)$_2$, —PO($R^3$)$_2$ and —O$Z^1$ in which R, $R^3$, X and $Z^1$ are as hereinbefore defined except for cis(±)4-acetyloxy-6-acetyloxymethyl tetrahydropyran-2-one.

According to a further feature of the present invention there is provided a resolved dihydropyran-2-one of Formula (2):

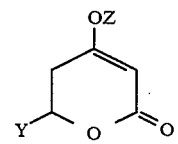

Formula (2)

wherein:

Z is —H or a protecting group; and

Y is $C_{1-3}$-hydrocarbyl optionally substituted by —CN, —Cl, —Br, —F, —I, azide, —OR, —SR, —P($R^3$)$_3$+X−, —PO(O$R^3$)$_2$, —PO($R^3$)$_2$ and —O$Z^1$ in which R, $R^3$, X and $Z^1$ are as hereinbefore defined provided that Z is not —H when Y is —CH$_3$.

A preferred resolved dihydropyran-2-one of Formula (2) is of the Formula (11):

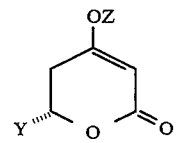

Formula (11)

wherein:

Z is —H or a protecting group; and

Y is $C_{1-3}$-hydrocarbyl optionally substituted by —CN, —Cl, —Br, —F, —I, azide, —OR, —SR, —P($R^3$)$_3$+X−, —PO(O$R^3$)$_2$, —PO($R^3$)$_2$ and —O$Z^1$ in which R, $R^3$, X and $Z^1$ are as hereinbefore defined provided that Z is not —H when Y is —CH$_3$.

A further preferred resolved dihydropyran-2-one of Formula (2) is of the Formula (12):

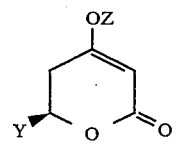

Formula (12)

wherein:

Z is —H or a protecting group; and

Y is $C_{1-3}$-hydrocarbyl optionally substituted by —CN, —Cl, —Br, —F, —I, azide, —OR, —SR, —P($R^3$)$_3$+X−, —PO(O$R^3$)$_2$, —PO($R^3$)$_2$ and —O$Z^1$ in which R, $R^3$, X and $Z^1$ are as hereinbefore defined provided that Z is not —H when Y is —CH$_2$Obenzyl or —CH$_3$.

According to a further feature of the present invention there is provided a racemate of dihydropyran-2-ones of Formula (2) wherein Z is —H or a protecting group; and Y is $C_{1-3}$-hydrocarbyl optionally substituted by —CN, —Cl, —Br, —F, —I, azide, —OR, —SR, —PO(OR$^3$)$_2$, —PO(R$^3$)$_2$ and —OZ$^1$ in which R, R$^3$, X and Z$^1$ are as hereinbefore defined provided that Z is not —H when Y is —CH$_2$Obenzyl or —CH$_3$.

A preferred sub group of racemic and resolved dihydropyran-2-ones of Formula (2) and resolved dihydropyran-2-ones are of Formulae (11) and (12) those in which Z is —H or a protecting group; and Y is $C_{1-3}$-hydrocarbyl optionally substituted by —CN, —Cl, —Br, —F, —I, azide, —OR, —SR, —P(R$^3$)$_3$+X$^-$, —PO(OR$^3$)$_2$, —PO(R$^3$)$_2$ and —OZ$^1$ in which R, R$^3$, X and Z$^1$ are as hereinbefore defined.

According to a further feature of the present invention there is provided a pyran-2-one of the Formula (3):

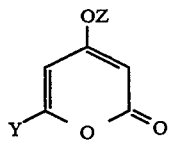

Formula (3)

wherein:
Z is —H or a protecting group; and
Y is $C_{1-3}$-hydrocarbyl optionally substituted by —CN, —Cl, —Br, —F, —I, azide, —OR, —SR, —P(R$^3$)$_3$+X$^-$, —PO(OR$^3$)$_2$, —PO(R$^3$)$_2$ and —OZ$^1$ in which R, R$^3$, X and Z$^1$ are as hereinbefore defined provided that Z is not —CH$_3$; or Z is not —H when Y is —CH$_2$Br, —CCl$_3$, —CH$_3$ or —CH$_2$OH; or that Y is not —CH$_2$P+Ph$_3$Br$^-$ when Z is —H, —COCH$_3$ or —COBu$^t$.

A preferred sub group of pyran-2-ones of Formula (3) are those in which Z is —H or a protecting group; Y is —CH$_2$CN, —CH$_2$OR, —CH$_2$SR, —CH$_2$P(R$^3$)$_3$+X$^-$, —CH$_2$PO(OR$^3$)$_2$, —CH$_2$PO(R$^3$)$_2$ and —CH$_2$OZ$^1$ in which R, R$^3$, X$^-$ and Z$^1$ are as hereinbefore defined.

According to a further feature of the present invention there is provided a pyran-2-one of Formula (4):

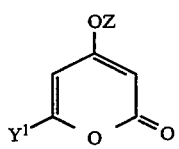

Formula (4)

wherein:
Y$^1$ is hydrocarbyl substituted by halogen; and
Z is —H or a protecting group,
provided that when Z is —H, Y$^1$ is not —CH$_2$Br.

A preferred sub group of pyran-2-ones of the Formula (4) are those in which Z is —H or a protecting group Y$^1$ is —CH$_2$Cl, —CH$_2$I, —(CH$_2$)$_2$Br, —(CH$_2$)$_2$Cl, —(CH$_2$)$_2$Br.

According to a further feature of the present invention there is provided a pyran-2-one of Formula (5):

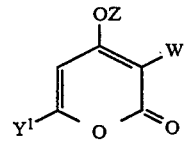

Formula (5)

wherein:
Y$^1$ is hydrocarbyl substituted by halogen;
Z is —H or a protecting group; and
W is —COT in which T is an optionally substituted hydrocarbon group, —CX$_3$, —CHX$_2$, or —CH$_2$X in which X is halogen,
provided that when Z is —H, Y is not —CH$_2$Br and W is not —COCH$_3$.

A preferred sub group of compounds of Formula (5) are those in which Z is —H or a protecting group; Y$^1$ is —CH$_2$Cl, —CH$_2$I, —(CH$_2$)$_2$Br, —(CH$_2$)$_2$Cl or —(CH$_2$)$_2$I; and W is —COCH$_3$, —COCH$_2$Cl, —COCH$_2$Br.

According to a further feature of the present invention there is provided a pyran-2-one of Formula (6):

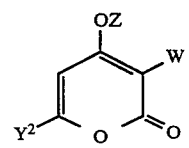

Formula (6)

wherein:
Y$^2$ is unsubstituted hydrocarbyl;
Z is —H or a protecting group; and
W is —COT in which T is an optionally substituted hydrocarbon group, —CX$_3$, —CHX$_2$ or —CH$_2$X in which X is halogen,
provided that when Z is —H; Y$^2$ is not —CH$_3$; and W is not —COCH$_3$.

A preferred sub group of compounds of Formula (6) are those in which Z is —H or a protecting group; Y$^2$ is —C$_2$H$_5$; and W is —COCH$_3$, —COCH$_2$Cl or —COCH$_2$Br.

A further preferred substituted group of compounds of Formula (6) are those in which Z is —H or a protecting group; Y is —CH$_3$ or —C$_2$H$_5$; and W is —COCH$_2$Cl or —COCH$_2$Br.

The invention is further illustrated by the following examples:

Example 1

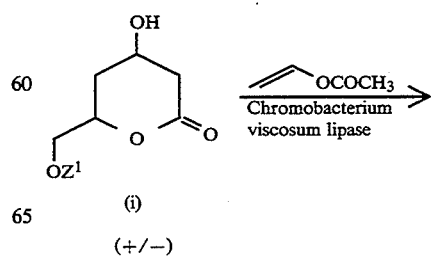

(i)
(+/−)

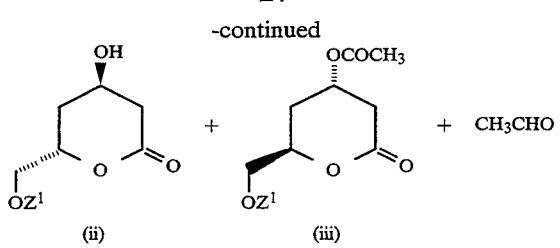

in which $Z^1$ is t-butyldimethylsilyl.

Tetrahydrofuran (3 cm³, BDH), containing the equilibrium amount of water picked up from the atmosphere during storage, was dissolved in vinyl acetate (6 cm³, Aldrich) in a 25 cm³ screw-top flask and 1 cm³ of a 0.384M solution of racemic trans Compound (i) in tetrahydrofuran was added. To this solution was added 50 mg of a lyophilised powder of Chromobacterium viscosum lipase (from Biocatalysts). The reaction mixture was shaken on an orbital shaker and heated to 40° C. for 8 hours. At this point capillary GC analysis showed that only about 50% of the initial amount of Compound (i) remained the rest having been converted to an equivalent amount of Compound (iii). The enzyme was then filtered from the reaction by passing the reaction mixture through filter paper, and removing the volatile liquids under reduced pressure on a rotary evaporator.

The resolved alcohol, Compound (ii), was separated from the ester, Compound (iii), by column chromatography (silica gel 60), eluting the mixture with 90:10 dichloromethane/ethyl acetate followed by 50:50 ethyl acetate/dichloromethane. The appropriate fractions were combined and the solvent removed in vacuo on a rotary evaporator. The resolved alcohol, Compound (2), was shown to be >95% e.e. by capillary gas chromatography using a cyclodextrin B-236-M.19 stationary phase (SGE Ltd). The chemical purity was 95%, giving a yield of 40% based on starting material.

The Compound (2) was characterised by ¹HNMR, ¹³CNMR and mass spectroscopy and optical rotation of the corresponding 3,4-dehydration product.

Example 2

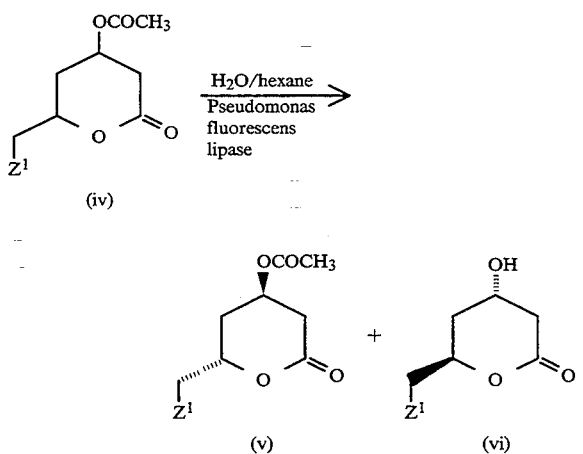

$Z^1$ is t-butyldimethylsilyl

To a stirred biphasic solution containing potassium phosphate buffer (30 cm³ of 10 mM) pH 7.0 and n-hexane (15 cm³) at 28° C. in an autotitrator of 60:40 cis:trans mixture of (±)4-acetoxy-6-t-butyl dimethylsilyloxymethyltetrahydropyran-2-one (0.24 g) were dissolved. After 13 minutes equilibration period Pseudomonas fluorescens lipase powder (0.2 g, Biocatalysts) was added and dissolved. The pH of the solution was maintained at 7.0 by automatic addition of 100 mM sodium hydroxide solution, the volume of sodium hydroxide added was recorded as a function of time allowing the progress of the reaction to be monitored. 4 cm³ Samples were withdrawn at 36, 72 and 150 minutes and these were analysed by gas chromatography. At 150 minutes the reaction was considered complete as there was no further addition of sodium hydroxide. The reaction mixture was worked up by evaporating the hexane solvent under reduced pressure, then extracting the reaction products from the aqueous layer into 3×1 volume equivalent of ethyl acetate. The ethyl acetate solution was dried over sodium sulphate and the solvent vacuum distilled to give 70% yield of the mixed alcohol and acetoxy products. Chiral gas chromatographic analysis showed the acetoxy Compound (v) to be >90% ee and the alcohol Compound (vi) to be >80% ee.

Example 3

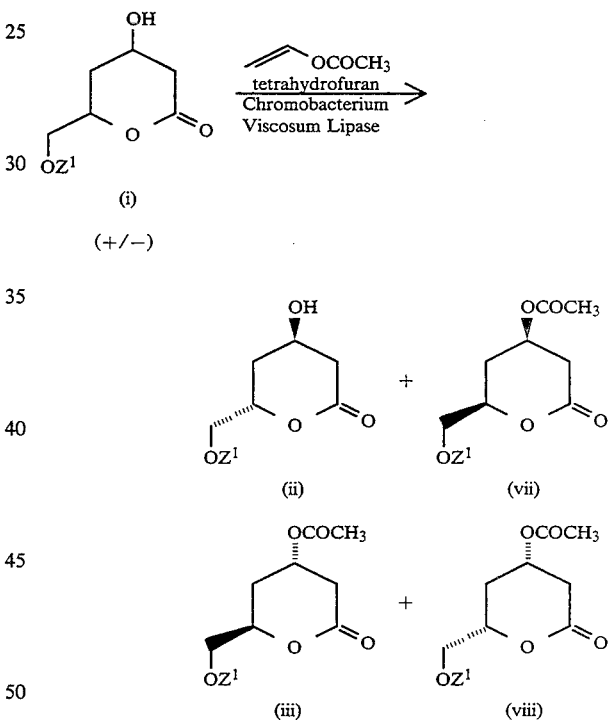

in which $Z^1$ is t-butyldimethylsilyl

Compound (i) (18.249 g, 0.07 moles) being a mixture of both the cis and trans racemates in the ratio 3:1 was dissolved in tetrahydrofuran (400 cm³) (used without any drying procedure), vinyl acetate (800 cm³) was added and the solution maintained at 40° C. The reaction was started by adding Chromobacterium viscosum lipase (2.74 g, Biocatalysts) while stirring the mixture. The reaction mixture was divided into 6×250 cm³ flasks, each sealed with a stopper and then placed on an orbital shaker at 40° C. for 150 hours. During the reaction 0.5 cm³ aliquots were taken at 5 hourly intervals and diluted 1:1 (v/v) with tetrahydrofuran containing a known amount of pentadecane internal standard to allow quantitative analysis of the reaction by gas chromatography. The sample was passed through a 0.2 μm millipore filter to remove the enzyme and injected onto a Perkin Elmer 8500 series gas chromatograph fitted with a 30 m×0.25 μm DB5 capilliary column (J and W Ltd) where both starting material and product cis and trans isomers were separated. The results of this analysis were plotted on a graph as a function of time so that the reaction could be followed. It was found that the cis enantiomers were esterified at a faster rate than the trans-enantiomers and that only 50% of the racemic trans was esterified. At the end of the reaction the enzyme was removed by filtering the solutions through paper. The volatile solvents were removed by vacuum distillation on the rotary evaporator, to yield a yellow oil. The yellow oil was chromatographed on silica using a mixture of dichloromethane and ethylacetate as eluent to give 1.82 g, 80% of the alcohol (ii) which was shown to be >95% e.e. by chiral GC.

A total of 14.84 g of the three isomers (iii), (vii) and (viii) was recovered.

Example 4

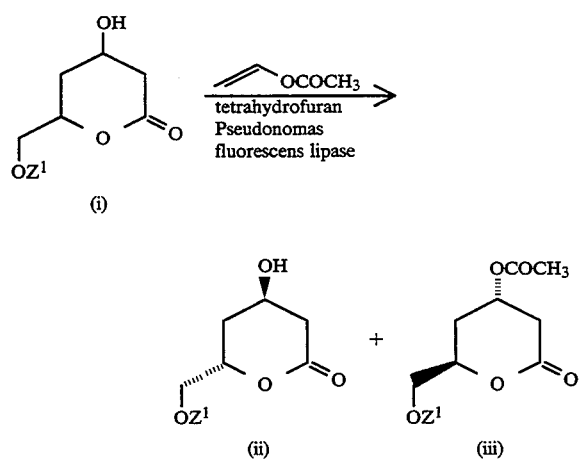

in which $Z^1$ is t-butyldimethylsilyl.

Compound (i) (5.0 g, 0.0192 moles) being a mixture of both the cis and trans racemates in the ratio 6:94 respectively, was dissolved in tetrahydrofuran (170 cm$^3$) used without any drying procedure. To this mixture vinyl acetate (340 cm$^3$) was added and solution warmed to 40° C. in a 1 liter screw topped flask. The reaction was initiated by adding Pseudomonas fluorescens lipase (3 g, Biocatalysts) while stirring the mixture. The reaction mixture was placed on an orbital shaker at 40° C. for 168 hours. During the reaction 0.5 cm$^3$ aliquots were taken at 5 hourly intervals and diluted 1:1 with tetrahydrofuran containing a known amount of pentadecane internal standard allowing quantitative analysis of the reaction by passing the sample through a 0.22 μm millipore filter to remove the enzyme and injection onto a Perkin Elmer 8500 series gas chromatograph fitted with a 30 m×0.25 μm DB5 capillary column (J and W Ltd). Using this method the extent of the reaction was determined and hence the end point of the reaction ascertained. At the end of the reaction the enzyme was removed by filtering the solution through paper. The volatile liquids were removed by vacuum distillation on a rotary evaporator to yield a yellow oil. The yellow oil was chromatographed on Silica C60 using a mixture of dichloromethane and ethyl acetate as eluent to give 1.8 g, 76% of the theoretical yield of the resolved alcohol (1). The alcohol (ii) was shown to be 99.4% e.e. by high field NMR using a chiral shift reagent (Europium tris D,D-dicamphorylmethanate).

Example 5

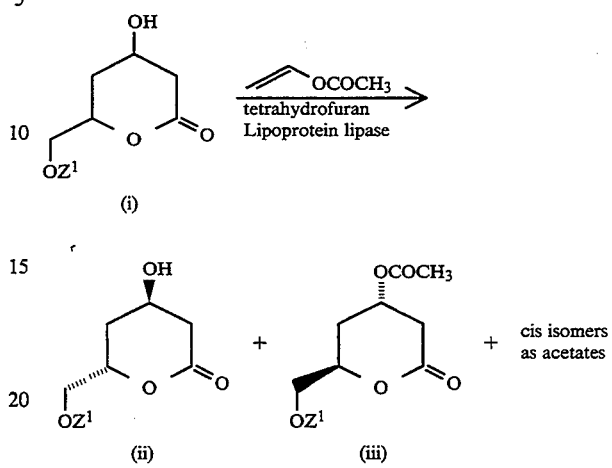

in which $Z^1$ is t-butyldimethylsilyl

Compound (i), (0.1 g, 3.846×10$^{-4}$ moles) being a mixture of the cis and trans racemates in the ratio 73:27 respectively, was dissolved in tetrahydrofuran (3 cm$^3$) used without any drying procedure. To this solution vinyl acetate (6 cm$^3$) was added and the solution warmed to 40° C. in a 25 cm$^3$ screw topped flask. The reaction was started by adding Lipoprotein lipase (12.5 mg, Boehringer Mannheim GmbH) while stirring the mixture. The reaction mixture was placed on an orbital shaker at 40° C. for 24 hours. At the end of the reaction the enzyme was removed by filtration the volatile solvents were removed under reduced pressure using a rotary evaporator. The resulting oil was analysed by chiral gas chromatography using a cyclodextrin B-236-M.19 stationary phase (SGE Ltd). The alcohol (ii) product was found to be >95% e.e.

Example 6

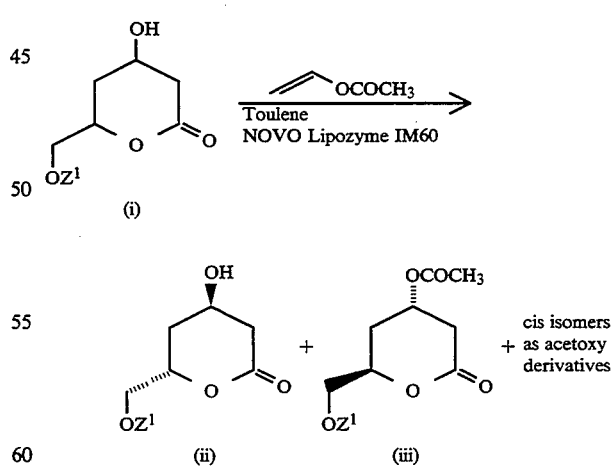

in which $Z^1$ is t-butyldimethylsilyl

Compound (i) (0.1 g, 3.846×10$^{-4}$ moles), a mixture of the cis and trans racemates in the ratio 73:27 respectively, was dissolved in of toluene (3 cm$^3$) used without any drying procedure. To this solution vinyl acetate (6 cm$^3$) was added and the solution warmed to 60° C. in a 25 cm$^3$ screw topped flask. The reaction was started by adding 400 mg of the polymer supported lipase Lipozyme IM60 (NOVO Industrie). The reaction mixture was placed on an orbital shaker at 60° C. for 24 hours. At the end of the reaction the enzyme was removed by filtration and the volatile solvents were removed under reduced pressure using a rotary evaporator. The resulting oil was analysed by chiral gas chromatography using a cyclodextrin B-236-M.19 stationary phase (SGE Ltd). The alcohol product (ii) was found to be 44% e.e.

Example 7

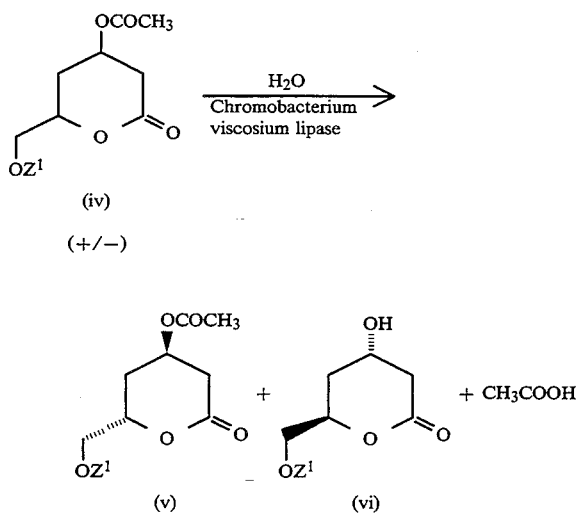

in which $Z^1$ is t-butyldimethylsilyl.

Potassium phosphate buffer (30 cm³ of 10 mM), pH 6.95, was added to of hexadecane (15 cm³) in a 100 cm³ stirred and thermostated flask fitted with a pH titrimeter containing NaOH solution. The titrimeter was set to maintain the pH in the flask at 7.0 by the addition of NaOH solution. 136 mg Of racemic Compound (iv) were added to the flask to give a 0.01M solution in the reaction medium. The medium was warmed to 40° C., 50 mg of Chromobacterium viscosum lipase (Biocatalysts) were added and the uptake of 0.1M NaOH recorded. As the reaction neared 50% conversion, i.e. when almost 50% of the racemic Compound (iv) had been hydrolysed, the uptake of NaOH slowed until, at 50% of the theoretical uptake, the reaction stopped. The reaction medium contained Compound (v) and Compound (vi) which are separable by the column chromatography method described in Example 1.

Example 8

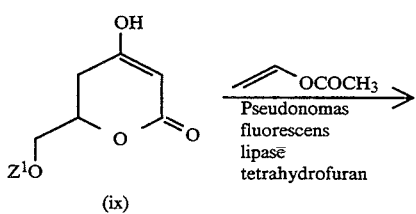

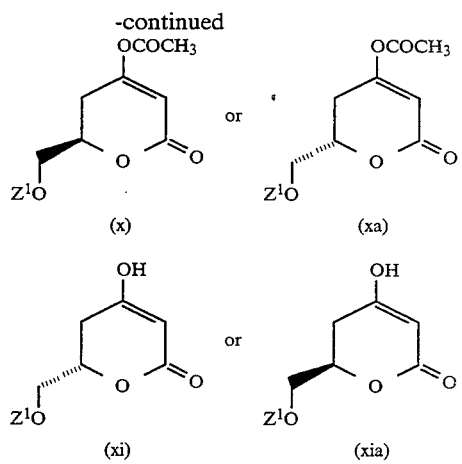

$Z^1$ is t-butyldimethylsilyl

Compound (ix) (232 mg, 0.992×10⁻⁴ moles) was dissolved in a 1:2 mixture of tetrahydrofuran:vinyl acetate (25 cm³). The solvents were used without any special drying procedure. Pseudomonas fluorescens lipase powder (250 mg, Biocatalysts) was added and the mixture was sealed in a 50 cm³ flask and shaken at 200 rpm at 40° C. for 72 hours. The reaction was monitored using Gas Chromatography and after 72 hours 39% of the starting material was consumed. The reaction mixture was filtered to remove the enzyme and the volatile solvents were evaporated under reduced pressure to leave a residue. The residue was derivatised and analysed by gas chromatography.

A mixture of (x) and (xi) or a mixture of (xa) and (xia) was obtained, the absolute stereochemistry of the products was not established. The alcohol (xi) or (xia) was found to be >90% ee.

Example 9

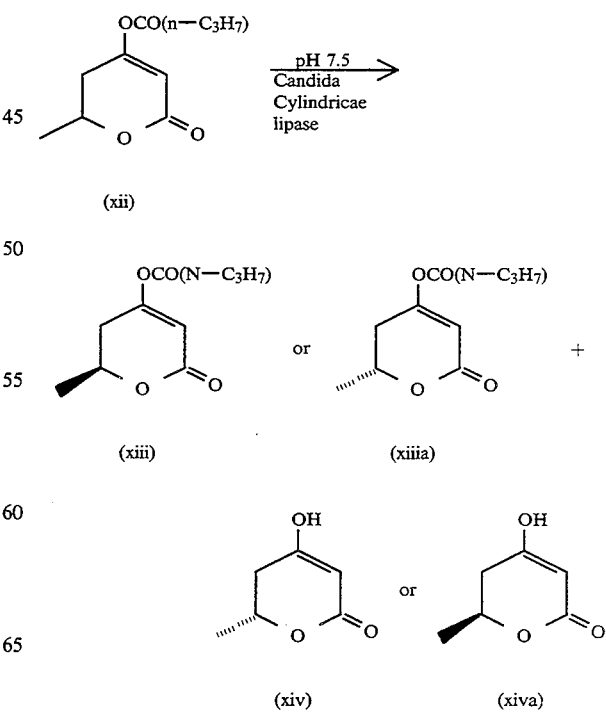

A mixture of Compound (xii) (200 mg, 1.01×10⁻³ moles), trihydroxymethylaminomethane buffer pH 7.5 (30 cm³, 100 mM), calcium chloride (20 mM) and Candida cylindracae lipase (5 mg, Biocatalysts) was stirred vigorously. The reaction was monitored by uptake of 0.25M sodium hydroxide solution whilst maintaining the pH at 7.5. When millimole of sodium hydroxide had been added, ethylacetate (15 cm³) was added to the reaction mixture which was stirred for 30 minutes. The organic layer was separated, dried (anhydrous sodium sulphate) and analysed by chiral gas chromatography.

A mixture of (xiii) and (xiv) or a mixture of (xiiia) and (xiva) was obtained, the absolute stereochemistry of the products was not established. The alcohol (xiv) or (xiva) was found to be 44% ee.

Example 10

Preparation of
3-acetyl-6-bromomethyl-4-hydroxypyran-2-one

A mixture of 3-acetyl-4-hydroxy-6-methylpyran-2-one (52 parts), N-bromosuccinimide (54 parts) and dichloromethane (1060 parts) were stirred at 20°–25° C. for about 4–5 hours under exposure to UV light. The dichloromethane solution was washed with water (2×500 cm³) to remove the succinimide, dried over magnesium sulphate, filtered and the solvent removed at 40° C./20 mm to leave 3-acetyl-6-bromomethyl-4-hydroxypyran-2-one (70 parts, 47%).

Example 11

Preparation of 6-bromomethyl-4-hydroxypyran-2-one

A mixture of 3-acetyl-6-bromomethyl-4-hydroxypyran-2-one (26 parts) and 90% sulphuric acid (73.4 parts) was heated at 125°–130° C. with rapid agitation for 20 minutes, then poured onto ice. The product was filtered off and washed with water (2×100 parts) and dried to give 6-bromomethyl-4-hydroxypyran-2-one (25.0 parts). The crude product was recrystallised from boiling chloroform to give 6-bromomethyl-4-hydroxy pyran-2-one (12.8 parts, 60%) melting point 77°–78° C.

Example 12

Preparation of 4-hydroxy-6-hydroxymethylpyran-2-one

6-Bromomethyl-4-hydroxypyran-2-one (21.1 parts) was dissolved in a solution of sodium hydroxide (4.1 parts) in water (800 parts) at 20°–25° C. This solution was added over about 2 hours to a solution of sodium hydroxide (34.2 parts) in water (3200 parts) at 50° C.±3° C. The mixture was stirred for a further hour at 50° C. before acidifying with 35% hydrochloric acid and distilling off the bulk of the water at 50° C./20 mm. The mixture was cooled to 20° C. and insoluble material was filtered off. The filtrate was saturated with sodium chloride and then extracted with ethyl acetate (15×125 parts). The combined extracts were dried over magnesium sulphate and the solvent removed at 40° C./20 mm to give 4-hydroxy-6-hydroxymethylpyran-2-one (10.2 parts, 69%).

Example 13

Preparation of
6-(t-butyldimethylsilyloxy)methyl-4-hydroxypyran-2-one

4-Hydroxy-6-hydroxymethylpyran-2-one (14.6 parts) was dissolved in dimethyl formamide (30 parts) at 20° C., imidazole (17.2 parts) was added and the temperature of the mixture cooled to 13° C. t-Butyldimethylsilyl chloride (17.1 parts) was then added in portions, the temperature was allowed to rise to 25° C. and maintained at 25°–30° C. by external cooling. The mixture was stirred for a further hour at 25°–30° C., before pouring into water (1100 parts) and stirring for 30 minutes until the product crystallised. The product was filtered off, washed with water (2×200 parts) and dried at 40° C./20 mm to give 6-t-butyldimethylsilyloxymethyl-4-hydroxy pyran-2-one (12.1 parts, 47%) m.pt 139°–141° C. Extraction of the filtrates with dichlorometane gave a further 7.0 parts, 27% of the product.

Example 14

Preparation of
6-(t-butyldimethylsilyloxy)methyl-5,6-dihydro-4-hydroxy pyran-2-one 6-t-Butyldimethylsilyloxymethyl-4-hydroxypyran-2-one (25.9 parts) was dissolved in ethanol (1600 parts) and the solution purged with nitrogen. 10% Palladium on carbon catalyst (5.2 parts) was added and the mixture hydrogenated at 20°–25° C. When the reaction was complete as judged by GC analysis the catalyst was filtered off and the solvent was distilled off under reduced pressure at 40° C. to leave 6-t-butyldimethylsilyloxymethyl-5,6-dihydro-4-hydroxy pyran-2-one (23.0 parts, 90%) m.p. 119°–122° C. as a light brown residue.

Example 15

Preparation of
6-(t-butyldimethylsilyloxy)methyl-4-hydroxytetrahydro pyran-2-one 6-t-Butyldimethylsilyloxymethyl-5,6-dihydro-4-hydroxy pyran-2-one (26.3 parts) was dissolved in ethanol (500 parts) and heated to 45° C.–55° C. Raney nickel (6.6 parts) was washed caustic free with water and then water free with ethanol and added to the pyran-2-one solution under a blanket of nitrogen. Hydrogen was passed through the rapidly stirred mixture until the reaction was complete, as judged by GC analysis. The catalyst was filtered off and the solvent removed at 40° C./20 mm to leave 6-t-butyldimethylsilyloxymethyl-4-hydroxytetrahydro pyran-2-one (25.7 parts, 96%, cis/trans ratio 82/18) as a greenish oil which solidified on standing.

Example 16

Chromatographic separation of the cis/trans isomers of 6-t-butyldimethyl silyloxymethyl-4-hydroxytetrahydropyran-2-one Crude 6-t-butyldimethylsilyloxymethyl-4-hydroxytetrahydro pyran-2-one (21 parts) was dissolved in diethylether (21 parts) and eluted down a 21"×3" column packed with Silica Gel 60 (230–400 mesh) using diethylether as eluent. The impurities present eluted first, then the trans isomers eluted followed by the cis isomers.

The following fractions were obtained:

| | |
|---|---|
| Impurities | (7.4 parts), |
| Trans | (4.0 parts, 99.3% trans, 0.7% cis), |
| Intermediate Fraction 1 | (3.6 parts, 54.7% trans, 45.3% cis), |
| Intermediate Fraction 2 | (4.2 parts, 16.6% trans, 83.4% cis), |
| Cis | (2.0 parts, 100% cis) |

Example 17

Preparation of
6-t-butyldimethylsilyloxymethyl-4-hydroxytetrahydro
pyran-2-one

To 6-butyldimethylsilyloxymethyl-4-hydroxypyran-2-one (20 parts) in ethanol (300 parts) was added alkali-free, ethanol washed Raney nickel (5 parts). Hydrogen gas was bubbled, at atmospheric pressure, through the rapidly stirred mixture which was held at 50°-55° C. When GLC analysis showed that the reduction was complete, the cooled reaction mixture was filtered and evaporated to give 6-t-butyldimethyl silyloxymethyl-4-hydroxytetrahydropyran-2-one (18.8 parts with a 77:23 cis:trans isomer ratio).

Example 18

Preparation of
6-t-butyldimethylsilyloxymethyl-4-hydroxytetrahydro
pyran-2-one (i) To 6-t-butyldimethylsilyloxymethyl-4-hydroxypyran-2-one (14.8 parts) in ethanol (800 parts) was added 10% palladium on carbon catalysts (2 parts) as an ethanol slurry. The mixture was hydrogenated at 25° C. for 1 hour when GLC analysis indicated complete reduction to 6-t-butyldimethylsilyloxymethyl-5,6-dihydro-4-hydroxy-pyran-2-one. At this stage the catalyst was filtered off and the volume reduced by evaporation under reduced pressure.

(ii) Raney nickel (4 parts), which had been washed alkali-free and then water-free with ethanol, was added before heating the reaction mixture to 50° C. and continuing the hydrogenation at 50°-60° C., until GLC examination showed that reduction of the dihydropyran-2-one was complete.

The catalyst was filtered off and the solvent removed by evaporation under reduced pressure to give 6-t-butyldimethylsilyl oxymethyl-4-hydroxytetrahydropyran-2-one (14.4 parts) 74:26 cis:trans ratio.

Example 19

Preparation of
4-acetoxy-6-t-butyldimethylsilyloxymethyl-5,6-dihydro
pyran-2-one To 6-t-butyldimethylsilyloxymethyl-5,6-dihydro-4-hydroxy-pyran-2-one (0.26 parts) in dichloromethane (3 cm$^3$) at ambient temperature was added pyridine (0.1 parts) and then acetyl chloride (0.1 parts). After approximately 30 minutes at ambient temperature the reaction mixture was washed with water, dried over MgSO$_4$ and evaporated to yield 4-acetoxy-6-t-butyldimethylsilyloxymethyl-5,6-dihydropyran-2-one (0.2 parts).

Example 20

Preparation of
6-t-butyldimethylsilyloxymethyl-4-butyryloxy-5,6-
dihydro pyran-2-one To a solution of 6-t-butyldimethylsilyloxymethyl-5,6-dihydro-4-hydroxy-pyran-2-one (7 parts) in dichloromethane (60 parts) was added pyridine (2.4 parts), followed by a solution of butyryl chloride (3.2 parts) in dichloromethane (10 parts) during a period of 10 minutes, at ambient temperature. After a further 30 minutes, cold water (25 parts) was added with stirring to dissolve the separated solids. The organic layer was separated, given a further water wash, dried and evaporated at <40° C. under reduced pressure to give 6-t-butyldimethyl silyloxymethyl-4-butyryloxy-5,6-dihydropyran-2-one (8.2 parts, 91%).

Example 21

Preparation of 6-cyanomethyl-4-hydroxypyran-2-one

6-Bromomethyl-4-hydroxypyran-2-one (21.1 parts) was added to a rapidly stirred mixture of sodium cyanide (9.8 parts) and dimethyl formamide (100 parts), keeping the temperature at 25°-30° C. After 30 minutes the reaction mixture was cooled below 15° C. and acidified with concentrated HCl (13 parts), during the acidification N$_2$ was bubbled through the mixture and the off-gases were passed through a bleach/caustic soda scrubber.

The reaction mixture was then diluted with water (1000 parts) and the solution saturated with sodium chloride. The mixture was then extracted with ethylacetate (8×100 parts) and the ethylacetate extracts dried over magnesium sulphate. The dried solution was evaporated to obtain the crude product as an oil which was dissolved in a 50/50 vol/vol mixture of chloroform and ethanol (100 parts). Evaporation to low volume followed by addition of water caused the product to precipitate. The solid was filtered off, washed with a small amount of water and air dried to give 6-cyanomethyl-4-hydroxypyran-2-one, m.pt 82°-90° C.

Example 22

Preparation of
4-acetoxy-6-t-butyldimethylsilyloxymethyltetrahydro-
pyran-2-one

To 6-t-butyldimethylsilyloxymethyl-4-hydroxytetrahydropyran-2-one (0.50 parts) in dichloromethane (10 parts) at ambient temperature was added pyridine (0.20 parts) followed by a solution of acetylchloride (0.20 parts) in dichloromethane (2 parts). After 1 hour at 20°-25° C. less than 2% starting material remained by GLC analysis. The reaction mixture was then washed with water, dried over magnesium sulphate and evaporated to give 4-acetoxy-6-t-butyldimethylsilyloxymethyltetrahydro pyran-2-one (0.6 parts).

Example 23

Preparation of
6-t-butyldimethylsilyloxymethyl-5,6-dihydropyran-
2-one

To 6-t-butyldimethylsilyloxymethyl-4-hydroxytetrahydropyran-2-one (0.52 parts) in dichloromethane (40 parts) was added triethylamine (0.8 parts) and the solution was cooled to −50° C. To this solution was then added a solution of methanesulphonyl chloride (0.48 parts) in dichloromethane (8 parts) during a period of one minute. The reaction mixture was then stirred for 30 minutes at −50° C. before warming to ambient temperature. After a further 3 hours the solution was washed with water, dried over magnesium sulphate and evaporated to obtain 6-t-butyldimethylsilyloxymethyl-5,6-dihydropyran-2-one (0.4 parts).

Example 24

Preparation of
6-t-butyldimethylsilyloxymethyl-5,6-dihydropyran-2-one 6-t-Butyldimethylsilyloxymethyl-4-hydroxytetrahydropyran-2-one (1.0 parts) was dissolved in toluene and p-toluenesulphonic acid (0.1 parts) was added. The reaction mixture was heated at reflux with removal of water via a Dean and Stark apparatus. The cooled reaction mixture was then washed with water and evaporated to give 6-t-butyl dimethylsilyloxymethyl-5,6-dihydropyran-2-one (0.3 parts).

Example 25

Preparation of
4-mesyloxy-6-methyl-tetrahydropyran-2-one

To a solution of 4-hydroxy-6-methyltetrahydropyran-2-one (1.5 parts) in dichloromethane (40 parts) was added pyridine (1.1 parts) and then, over 15 minutes, mesyl chloride (1.65 parts). The reaction was set aside at ambient temperature under $N_2$ for 18 hours at which point GLC analysis indicated less than 1.5% of the starting material remained. The reaction mixture was filtered and the organic phase then washed with water before evaporating to obtain 4-mesyloxy-6-methyl-tetrahydropyran-2-one (0.5 parts).

Example 26

Preparation of
6-t-butyldimethylsilyloxymethyl-4-hydroxypyran-2-one:
4-t-butyldimethylsilyloxy-6-t-butyldimethylsilyloxymethylpyran-2-one The 4-hydroxy-6-hydroxymethylpyran-2-one' (0.7 parts) in dimethylformamide (2 parts) was added imidazole (1.7 parts) followed by t-butyldimethylsilyl chloride (1.8 parts). The temperature of the mixture rose from 23° C. to 37° C. following addition of the silyl chloride; it was then held at 35°–40° C. for a further 4 hours before pouring into water (25 parts) and extracting with dichloromethane. Evaporation of the solvent gave a 1:2 mixture of the mono and disilylated products: 6-(t-butyldimethylsilyloxymethyl)-4-hydroxypyran-2-one:4-(t-butyldimethylsilyloxy)-6-(t-butyldimethylsilyloxymethyl) pyran-2-one.

Example 27

Method for Chromatographic Separation of

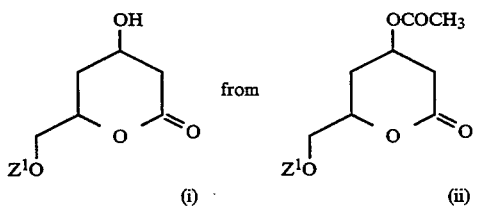

$Z^1$ is t-butyldimethylsily
i.e. for use after the biological resolution which produces mixtures of (I) and (II).

A mixture comprising, for example 0.9 parts of II and 0.1 parts of I is dissolved in a small amount of dichloromethane and then applied to an 8"×1" column of Silica Gel 60. Elution with dichloromethane removes (II), the solvent is then changed to diethylether to elute the hydroxylactone (I).

The method is applicable whether (I) and/or (II) is present as either the cis or trans isomer or as a cis-trans isomer mixture.

Example 28

Separation of product from bio-resolution process and its subsequent dehydration to confirm the absolute stereochemistry

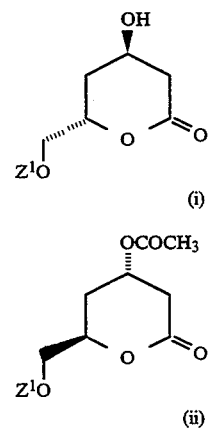

$Z^1$ is t-butyldimethylsilyl (i) An approximately equimolar mixture of the pyran-2-ones (ii) and (iii) (4.5 parts) in dichloromethane (3 parts) was eluted down a 17"×2" Silica Gel 60 column initially with dichloromethane and then with increasing proportions of ethylacetate in dichloromethane. Compound (II) eluted preferentially in the earlier fractions and compound (I) in the later, ethylacetate, fractions.

Monitoring by GLC analysis allowed fractions to be identified which contained substantially pure (ii) and (iii) respectively.

(ii) Pyran-2-one (ii) (0.45 parts), from the above chromatographic separation was dissolved in dichloromethane at 20° C. and triethylamine (0.7 parts) was added. The mixture was cooled to −50° C. before adding a solution of methanesulphonyl chloride (0.42 parts) in dichloromethane (5 parts). After holding at −50° C. for 15 minutes the mixture was warmed to room temperature and, after a further 2 hours, washed with water, dried and evaporated to give 6-(t-butyldimethylsilyloxymethyl)-5,6-dihyro pyran-2-one (0.4 parts) which had negative $[\alpha]_D^{20}$ (measured in $CHCl_3$) confirming the (6S) stereochemistry of (I).

Example 29

Preparation of
6-t-butyldimethylsilyloxymethyl-4-mesyloxytetrahydro pyran-2-one 6-t-Butyldimethylsilyloxymethyl-4-hydroxytetrahydropyran-2-one (1.0 part) was dissolved in dichloromethane (40 parts) and pyridine (5 parts). To this solution mesyl chloride (5 parts) was slowly added. The reaction was set aside at room temperature for 72 hours, during this period crystals of pyridinium chloride formed and these were removed by filtration. The filtrate washed twice with citrate phosphate buffer pH 6.0, the organic solvent was separated and dried over anhydrous sodium sulphate and evaporated to give 6-t-butyldimethylsilyloxymethyl-4-mesyloxytetrahydropyran-2-one (0.67 parts).

We claim:

1. A process for the separation of at least one isomer from a mixture of isomers of tetrahydropyran-2-one, having at least two chiral centres, which comprises selective reaction of at least one isomer with a reagent catalysed by a hydrolase enzyme selected from an esterase, lipase, nitrilase, amidase, peptidase, glycosidase and phosphatase derived from microbial, animal and plant sources whereby at least one isomer is preferentially converted into a distinct chemical species from the other isomers so that it is susceptible of separation by an appropriate chemical or physical separation process in which the tetrahydropyran-2-one is of Formula (1):

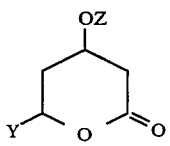

Formula (1)

wherein
- Z is —H or a protecting group susceptible of reaction with the reagent under the influence of the enzyme, said protecting group being selected from the group consisting of —$NO_2$; —$PO.(OR^3)_2$; —$CO.R^3$; —$SO.OR^3$; and —$CO.OR^3$ in which each $R^3$ independently is optionally substituted alkyl, optionally substituted alkenyl or optionally substituted phenyl; and
- Y is optionally substituted hydrocarbyl wherein when Z is —H the reagent is an ester or an acid capable of reacting with —OZ and when Z is a protecting group the reagent is water or an alkanol.

2. A process according to claim 1 wherein the mixture of isomers of a tetrahydropyran-2-one of Formula (1) is prepared by the reduction of a dihydropyran-2-one of Formula (2):

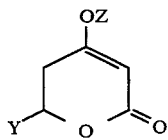

Formula (2)

wherein:
- Z is —H or a protecting group as defined in claim 1 susceptible of reaction with the reagent under the influence of the enzyme; and
- Y is optionally substituted hydrocarbyl.

3. A process according to claim 2 wherein the dihydropyran-2-one of Formula (2) is prepared by the reduction of a pyran-2-one of Formula (3):

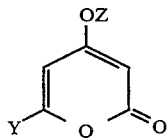

Formula (3)

wherein:
- Z is —H or a protecting group as defined in claim 1 susceptible of reaction with the reagent under the influence of the enzyme; and Y is optionally substituted hydrocarbyl.

4. A process according to claim 3 wherein the pyran-2-one of Formula (3) in which Y is hydrocarbyl substituted by —CN, —$N_3$, —OR, —SR in which R is —H, alkyl, alkenyl or phenyl; —$PO.(OR^3)_2$, —$PO.(R^3)_2$ or $P(R^3)_3{}^+X^-$ in which each $R^3$ is independently optionally substituted alkyl, optionally substituted alkenyl or optionally substituted phenyl; and $X^-$ is halide and Z is —H or a protecting group as defined in claim 1 susceptible of reaction with the reagent under the influence of the enzyme is prepared by reaction of a pyran-2-one of Formula (4):

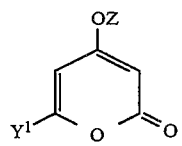

Formula (4)

wherein:
- $Y^1$ is hydrocarbyl substituted by halogen;
- Z is as hereinbefore defined with a compound of Formula MQ in which M is —H or metal; and Q is —CN, —$N_3$, —$CS_3$, —OR, —SR, in which R is as hereinbefore defined, or in which MQ is $P(OR^3)_3$, $(R^3)_2POR^3$ or $P(R^3)_3$ in which $R^3$ is as hereinbefore defined.

5. A process according to claim 4 wherein the pyran-2-one of Formula (4) is prepared by removal of a group W from a pyran-2-one of Formula (5):

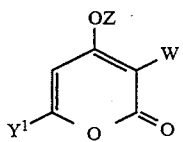

Formula (5)

wherein:
- $Y^1$ is hydrocarbyl substituted by halogen;
- Z is —H or a protecting group susceptible of reaction with the reagent under the influence of the enzyme, said protecting group being selected from the group consisting of —$NO_2$; —$PO.(OR^3)_2$; —$CO.R^3$; —$SO.OR^3$; and —$CO.OR^3$ in which each $R^3$ independently is optionally substituted alkyl, optionally substituted alkenyl or optionally substituted phenyl; and
- W is —$COC_{1-2}$-alkyl or —$COC_2$-alkenyl each of which is optionally substituted by halogen, —CN, —$OR^6$, or —$SR^6$ in which $R^6$ is —H, $C_{1-6}$-alkyl, $C_{2-12}$-alkenyl or phenyl.

6. A process according to claim 5 wherein the pyran-2-one of Formula (5) is prepared by halogenation of a pyran-2-one of Formula (6):

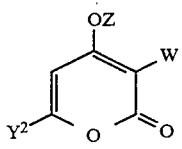

Formula (6)

wherein:
- $Y^2$ is unsubstituted hydrocarbyl;
- Z is —H or a protecting group as defined in claim 5 susceptible of reaction with the reagent under the influence of the enzyme; and W is —COC$_{1-2}$-alkyl or —COC$_2$-alkenyl each of which is optionally substituted by halogen, —CN, —OR$^6$, or —SR$^6$ in which R$^6$ is —H, C$_{1-6}$-alkyl, C$_{2-12}$-alkenyl or phenyl.

7. A process according to claim 1 wherein the mixture of isomers of a tetrahydropyran-2-one of Formula (1) is prepared by the reduction of a pyran-2-one of Formula (3):

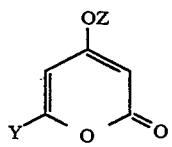

Formula (3)

wherein:
Z is —H or a protecting group as defined in claim 1 susceptible of reaction with the reagent under the influence of the enzyme; and
Y is optionally substituted hydrocarbyl.

8. A process according to any one of claims 1 to 7 wherein in the tetrahydropyran-2-one of Formula (1) Z is —H and the reagent is an ester of Formula R$^4$COOR$^5$ or an acid of Formula R$^4$COOH in which R$^4$ and R$^5$ each independently is optionally substituted alkyl, alkenyl or aryl.

9. A process according to any one of claims 1 to 7 wherein in the tetrahydropyran-2-one of Formula (1) Z is —COR$^4$ in which R$^4$ is optionally substituted alkyl, alkenyl or aryl and the reagent is water or a hydroxy compound of Formula ROH in which R is optionally substituted alkyl, alkenyl or aryl.

10. A process according to claim 4 wherein:
Z is —H or a protecting group as defined in claim 1 susceptible of reaction with the reagent under the influence of the enzyme;
Y is hydrocarbyl substituted by —CN, —N$_3$, —OCH$_2$Ph, —SCH$_2$Ph, —SH, —PO.(OPh)$_2$, —PO.(OEt)$_2$, —PO(Ph)$_2$, PPh$_3$+Br$^-$ or —P(CH$_2$Ph)$_3$+Br$^-$;
Y$^1$ is hydrocarbyl substituted by —Br;
M is —H, —Li, Na or K; and
Q is —CN, —N$_3$, —OCH$_2$Ph, —SCH$_2$Ph, —CS$_3$, —OH or MQ is P(OPh)$_3$, P(OEt)$_3$, (Ph)$_2$P(OPh), PPh$_3$ or P(CH$_2$Ph)$_3$.

11. A process according to claim 5 wherein:
Z is —H or a protecting group as defined in claim 1 susceptible of reaction with the reagent under the influence of the enzyme;
Y$^1$ is hydrocarbyl substituted by —Br; and
W is —COCH$_3$, —COCH$_2$Cl, —COCH$_2$Br, —COCHBr$_2$, —COCHCl$_2$.

12. A process according to claim 6 wherein:
Y$^2$ is C$_{1-3}$-hydrocarbyl;
Z is —H or a protecting group as defined in claim 1 susceptible of reaction with the reagent under the influence of the enzyme; and
W is —COCH$_3$.

13. A process according to claim 1 wherein said hydrolase enzyme is selected from Chromobacterium viscosum lipase, AMANO P lipase, Pseudomonas fluorescens lipase, Mucor miehi strain NOVO IM60, Mucor miehi strain NOVO lypozyme and Lipoprotein lipase from Pseudomonas species.

14. A process for the resolution of a mixture of enantiomers of a dihydropyran-2-ones of the Formula (2):

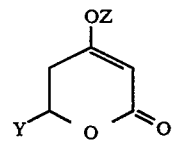

Formula (2)

which comprises a selective reaction of one enantiomer with a reagent catalysed by a hydrolase enzyme whereby the enantiomer is preferentially converted into a distinct chemical species from the other enantiomer so that it is susceptible of separation by an appropriate chemical or physical separation process, wherein:
Z is —H or a protecting group susceptible of reaction with the reagent under the influence of the enzyme; and Y is optionally substituted hydrocarbyl, selected from the group consisting of —NO$_2$; —PO.-(OR$^3$)$_2$; —CO.R$^3$; —SO.OR$^3$; and —CO.OR$^3$ in which each R$^3$ independently is optionally substituted alkyl, optionally substituted alkenyl or optionally substituted phenyl wherein when Z is —H the reagent is an ester or an acid capable of reacting with —OZ and when Z is a protecting group the reagent is water or an alkanol.

* * * * *